United States Patent
Shalgi et al.

(10) Patent No.: US 10,130,682 B2
(45) Date of Patent: Nov. 20, 2018

(54) METHODS OF USING PIGMENT EPITHELIUM DERIVED FACTOR (PEDF) FOR THE TREATMENT AND PREVENTION OF AGENT-INDUCED GONADAL OR UTERINE TOXICITY

(71) Applicants: Ramot at Tel-Aviv University Ltd., Tel-Aviv (IL); Mor Research Applications Ltd., Tel-Aviv (IL)

(72) Inventors: Ruth Shalgi, Herzlia (IL); Dana Chuderland, Ramat-HaSharon (IL); Hadas Bar-Joseph, Tel-Aviv (IL); Keren Goldberg, Tel-Aviv (IL); Irit Ben-Aharon, Hod-HaSharon (IL); Salomon M. Stemmer, Givat Shmuel (IL)

(73) Assignees: Ramot at Tel-Aviv University Ltd., Tel-Aviv (IL); Mor Research Applications Ltd., Tel-Aviv (IL)

( * ) Notice: Subject to any disclaimer, the term of this patent is extended or adjusted under 35 U.S.C. 154(b) by 0 days.

(21) Appl. No.: 15/129,007

(22) PCT Filed: Mar. 30, 2015

(86) PCT No.: PCT/IL2015/050340
§ 371 (c)(1),
(2) Date: Sep. 26, 2016

(87) PCT Pub. No.: WO2015/151091
PCT Pub. Date: Oct. 8, 2015

(65) Prior Publication Data
US 2017/0202916 A1    Jul. 20, 2017

Related U.S. Application Data

(60) Provisional application No. 61/972,325, filed on Mar. 30, 2014.

(51) Int. Cl.
*A61K 38/18* (2006.01)
*A61K 31/138* (2006.01)
*A61K 31/704* (2006.01)
*C12N 5/075* (2010.01)
*G01N 33/74* (2006.01)

(52) U.S. Cl.
CPC ............ *A61K 38/18* (2013.01); *A61K 31/138* (2013.01); *A61K 31/704* (2013.01); *C12N 5/0609* (2013.01); *G01N 33/74* (2013.01); *C12N 2501/10* (2013.01); *G01N 2333/475* (2013.01); *G01N 2800/34* (2013.01); *G01N 2800/36* (2013.01); *G01N 2800/52* (2013.01); *G01N 2800/709* (2013.01)

(58) Field of Classification Search
None
See application file for complete search history.

(56) References Cited

U.S. PATENT DOCUMENTS

| | | |
|---|---|---|
| 2003/0216286 A1 | 11/2003 | Bouck et al. |
| 2004/0071659 A1 | 4/2004 | Chang et al. |
| 2007/0087967 A1 | 4/2007 | Bouck et al. |
| 2009/0118191 A1* | 5/2009 | Volz ............... C07K 14/811 514/1.1 |
| 2013/0053312 A1* | 2/2013 | Shalgi ............ A61K 38/57 514/7.6 |

FOREIGN PATENT DOCUMENTS

| | | | |
|---|---|---|---|
| WO | WO2006/054278 | * 5/2006 | ........ C07K 14/475 |
| WO | WO 2011/058557 | 5/2011 | |
| WO | WO 2015/151091 | 10/2015 | |

OTHER PUBLICATIONS

Cheung et al., Endocrinology, 2006; 147: 4179-4191.*
Rodriguez-Wallberg and Oktay, Clinical Obstetrics and Gynecology, 2010; 53: 753-762. (Year: 2010).*
Phillips, A., J Pharm Pharmacology, 2001; 53: 1169-1174. (Year: 2001).*
Jafarlou et al., Journal of Biological Regulators & Homeostatic Agents, 2016: 30: 315-321. (Year: 2016).*
El-Missiry et al., Ecotoxicology and Environmental Safety, 2007; 66: 278-286. (Year: 2007).*
Jain, Nature Medicine, 2001; 7: 987-989 (Year: 2001).*
Clarke et al., The Lancet, 1998; 351: 1451-1467 (Year: 1998).*
Tutt et al., Lancet, 2010; 376: 235-244 (Year: 2010).*
Lewis-Wambi (Abstract 744: PEDF silencing a novel mechanism of antihormone resistance in breast cancer; In: Proceedings of the 102nd Annual Meeting of the American Association for Cancer Research; Cancer Res 2011;71(8 Suppl):Abstract nr 744. doi: 10.1158/1538-7445.AM2011-744 (Year: 2011).*
International Preliminary Report on Patentability dated Oct. 13, 2016 From the International Bureau of WIPO Re. Application No. PCT/IL2015/050340.

(Continued)

Primary Examiner — Christina M Borgeest

(57) ABSTRACT

A method of treating or preventing gonadal or uterine toxicity induced by an agent in a subject is provided. Accordingly there is provided a method comprising administering to a subject a therapeutically effective amount of pigment epithelium-derived factor (PEDF), thereby treating or preventing the gonadal toxicity induced by the agent. Also provided is, a method comprising determining gonadal function in a subject; and administering to the subject a therapeutically effective amount of PEDF, thereby treating or preventing the gonadal toxicity induced by the agent. Also provided is a PEDF for use in the treatment or prevention of gonadal toxicity induced by an agent in a subject. Also provided are cell culture, a medium, a kit and method for improving oocyte quality ex-vivo.

30 Claims, 20 Drawing Sheets
(3 of 20 Drawing Sheet(s) Filed in Color)
Specification includes a Sequence Listing.

(56) References Cited

OTHER PUBLICATIONS

International Search Report and the Written Opinion dated Jul. 21, 2015 From the International Searching Authority Re. Application No. PCT/IL2015/050340.
Invitation to Pay Additional Fees and Communication Relating to the Results of the Partial International Search dated Jun. 10, 2015 From the International Searching Authority Re. Application No. PCT/IL2015/050340.
American College of Obstetricians and Gynecologists "Tamoxifen and Uterine Cancer", The American College of Obstetricians and Gynecologists, Committee Opinion No. 601, Obstetrics & Gynecology, 123(6): 1394-1397, Jun. 2014.
Bar-Joseph et al. "Doxorubicin-Induced Apoptosis in Germinal Vesicle (GV) Oocytes", Reproductive Toxicology, 30: 566-572, Published Online Jul. 23, 2010.
Bar-Joseph et al. "In Vivo Bioimaging as a Novel Strategy to Detect Doxorubicin-Induced Damage to Gonadal Blood Vessels", PLoS ONE, 6(9): e23492-1-e23492-8, Sep. 9, 2011.
Bar-Joseph et al. "Pigment Epithelium-Derived Factor Exerts Antioxidative Effects in Granulosa Cells", Fertility and Sterility, 102(3): 891-898e-2, Sep. 2014.
Ben-Aharon et al. "Doxorubicin-Induced Ovarian Toxicity", Reproductive Biology and Endocrinology, 8(20): 1-7, Mar. 4, 2010.
Brydoy et al. "Gonadal Dysfunction and Fertility Problems in Cancer Survivors", Acta Oncologica, 46: 480-489, 2007.
Cheung et al. "Pigment Epithelium-Derived Factor Is Estrogen Sensitive and Inhibits the Growth of Human Ovarian Cancer and Ovarian Surface Epithelial Cells", Endocrinology, 147(9): 4179-4191, 2006.
Choong et al. "PEDF: A Potential Therapeutic Agent for Osteosarcoma", The Liddy Shriver Sarcoma Initiative, Study Report, 19 P., 2008. Figs.4-5.
Chuderland et al. "A Physiological Approach for Treating Endometriosis by Recombinant Pigment Epithelium-Derived Factor (PEDF)", Human Reproduction, 28(6): 1626-1634, Advanced Access Publication Mar. 6, 2013. Fig. 6b.
Chuderland et al. "Hormonal Regulation of Pigment Epithelium-Derived Factor (PEDF) in Granulosa Cells", Molecular Human Reproduction, MHR, 19(2): 72-81, 2013.
Chuderland et al. "The Role of Pigment Epithelium-Derived Factor in the Pathophysiology and Treatment of Ovarian Hyperstimulation Syndrome in Mice", The Journal of Clinical Endocrinology and Metabolism, 98(2): E258-E266, Feb. 2013.
Jan et al. "Loss of Pigment Epithelium-Derived Factor: A Novel Mechanism for the Development of Endocrine Resistance in Breast Cancer", Breast Cancer Research, 14(6): R146-1-R146-19, Nov. 14, 2012. Figs. 1, 2, 3b.
Jia et al. "Thrombospondin-1 and Pigment Epithelium-Derived Factor Enhance Responsiveness of KM12 Colon Tumor to Metronomic Cyclophosphamide But Have Disparate Effects on Tumor Metastasis", Cancer Letters, 330: 241-249, 2013.
Kampfer et al. "Pigment-Epithelium Derived Factor (PEDF) and the Human Ovary: A Role in the Generation of ROS in Granulosa Cells", Life Sciences, 97: 129-136, 2014.
Ma et al. "Combination of Anti-Angiogenesis With Chemotherapy for More Effective Cancer Treatment", Molecular Cancer Therapy, 7(12): 3670-3684, Dec. 2008.
Manalo et al. "Pigment Epithelium-Derived Factor as an Anticancer Drug and New Treatment Methods Following the Discovery of Its Receptors: A Patent Perspective", Expert Opinion on Therapeutic Patents, 21(2): 121-130, Feb. 2011.
Morgan et al. "Cisplatin and Doxorubicin Induce Distinct Mechanisms of Ovarian Follicle Loss; Imatinib Provides Selective Protection Only Against Cisplatin", PLOS ONE, 8(7): e70117-1-e70117-10, Jul. 29, 2013.
Nelius et al. Effect of PEDF on the In Vivo Antitumor Activities of Low-Dose Chemotherapy in CRPC, 2013 Genitourinary Cancers Sympsoium, General Poster Session A: Prostate Cancer, Journal of Clinical Oncology, 31(Suppl.6): # 173, 2013.
Palmieri et al. "Age-Related Expression of PEDF/EPC-1 in Human Endometrial Stromal Fibroblasts: Implications for Interactive Senescence", Experimental Cell Research, 247(1): 142-147, Feb. 25, 1999. Abstract.
Pollina et al. "Regulating the Angiogenic Balance in Tissues: A Potential Role for the Proliferative State of Fibroblasts", Cell Cycle, 7(13): 2056-2070, Jul. 1, 2008.
Yamagishi et al. "Pigment Epithelium-Derived Factor (PEDF) Blocks Angiotensin II Signaling in Endothelial Cells via Suppression of NADPH Oxidase: A Novel Anti-Oxidative Mechanism of PEDF", Cell and Tissue Research, 320(3): 437-445, Jun. 2005. Abstract.
Communication Pursuant to Rule 164(1) EPC [Supplementary Partial European Search Report and the Provisional Opinion] dated Dec. 22, 2017 From the European Patent Office Re. Application No. 15774029.1. (13 Pages).
Blumenfeld et al. "'An Ounce of Prevention is Worth a Pound of Cure': The Case for and Against GnRH-Agonist for Fertility Preservation", Annals of Oncology, XP055426972, 25(9): 1719-1728, Published Online Mar. 20, 2014. p. 1722-1726.

* cited by examiner

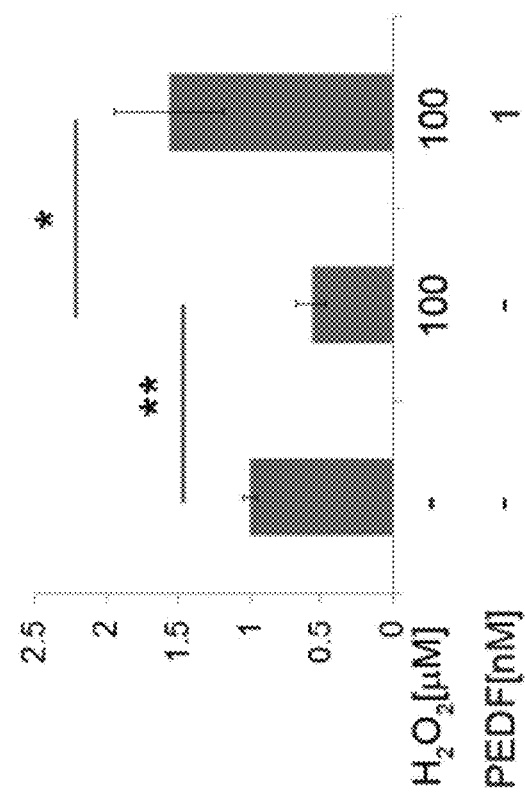
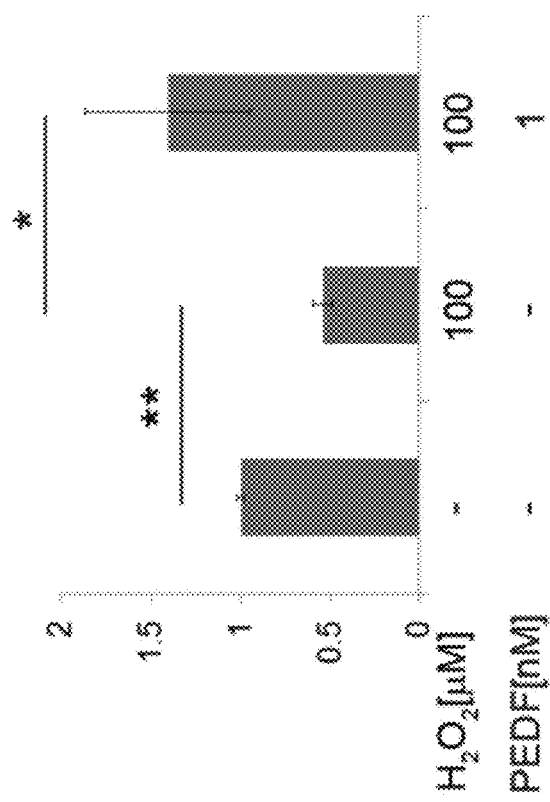

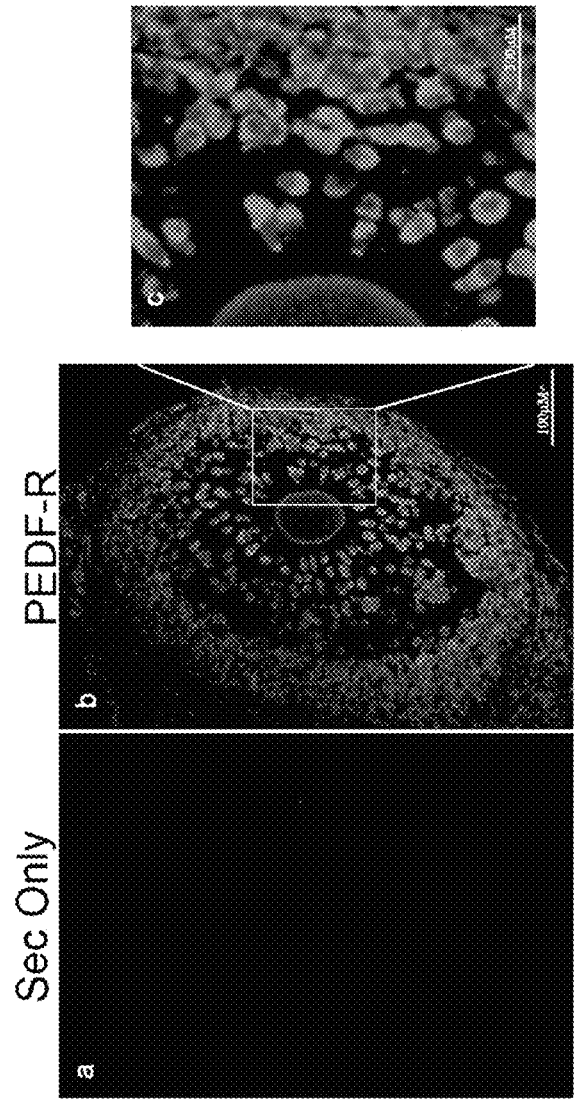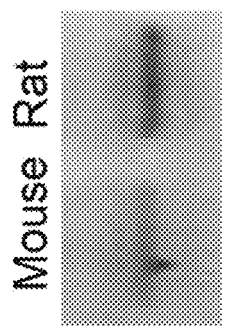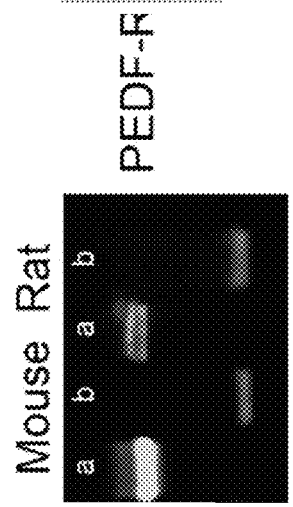
Figure 6A
Figure 6B
Figure 6C

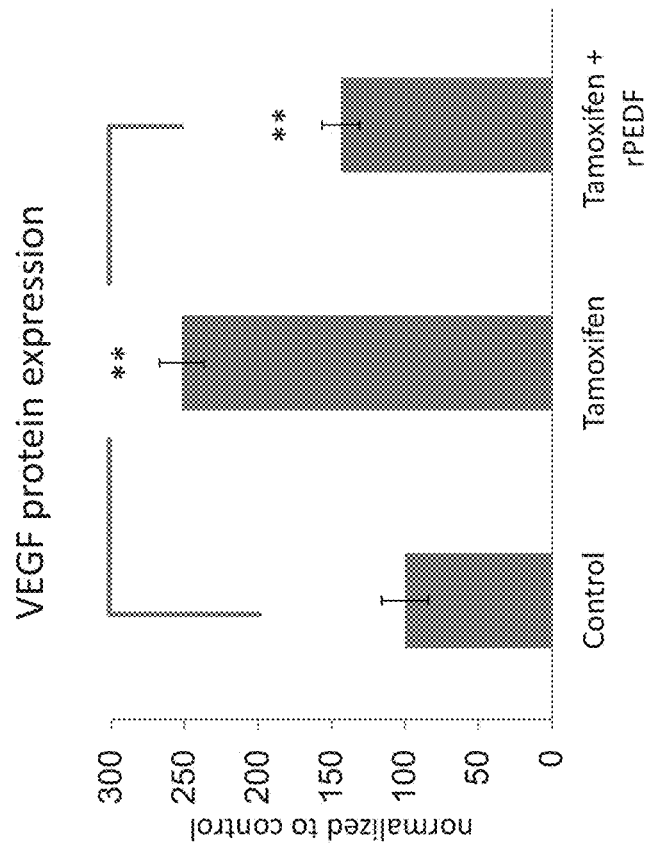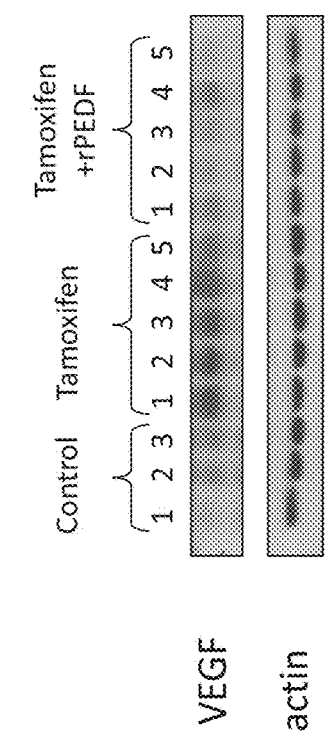
Figure 12A
Figure 12B

Uterine weight

VEGF protein expression

METHODS OF USING PIGMENT EPITHELIUM DERIVED FACTOR (PEDF) FOR THE TREATMENT AND PREVENTION OF AGENT-INDUCED GONADAL OR UTERINE TOXICITY

RELATED APPLICATIONS

This application is a National Phase of PCT Patent Application No. PCT/IL2015/050340 having International filing date of Mar. 30, 2015, which claims the benefit of priority under 35 USC § 119(e) of U.S. Provisional Patent Application No. 61/972,325 filed on Mar. 30, 2014. The contents of the above applications are all incorporated by reference as if fully set forth herein in their entirety.

SEQUENCE LISTING STATEMENT

The ASCII file, entitled 67674SequenceListing.txt, created on Sep. 30, 2015, comprising 65,176 bytes, submitted concurrently with the filing of this application is incorporated herein by reference.

FIELD AND BACKGROUND OF THE INVENTION

The present invention, in some embodiments thereof, relates to methods of using PEDF for the treatment and prevention of agent-induced gonadal or uterine toxicity.

Over the past three decades, there has been a remarkable improvement in the survival rates of cancer patients owing to progress in earlier stage diagnosis and improvements in treatment. As a consequence, greater attention has been focused on the delayed effects of cancer treatments on the life quality of healed subjects.

The treatment for most cancer types involves cytotoxic treatments such as chemotherapy and radiotherapy that may partially or definitively affect the reproductive function, hinder the hormonal milieu and gonadal reserve, and may subsequently induce either sterility or early menopause. The risk of gonadal and uterine toxicity following cancer therapy appears to be treatment and dose-dependent and age related. Thus, for example the use of Tamoxifen as an antagonist to estrogen receptor for the treatment of breast cancer, for example, results in an agonistic activity in the uterus that results in a range of endometrial pathologies including hyperplasia and endometrial cancer (Obstet Gynecol. 2014 June; 123(6):1394-7). Some of the chemotherapeutic agents e.g., doxorubicin (DXR), cyclophosphamide, busulfan and ifosfamide, which are frequently used for the treatment of various cancers including breast cancer, lymphomas, leukemia and sarcomas, are known to have irreversible gonadotoxic effects. Gonadal dysfunction following radiotherapy may occur when the gonads are close to or within the radiation field [Brydøy et al. Acta Oncologica (2007). 46: 480-489].

Gonadal dysfunction following cancer treatment has been attributed both to induction of vascular damage leading to ischemia and to direct acute insult to the gonads by apoptosis induction such as by induction of oxidative stress and increase in intracellular calcium [Ben-Aharon et al., Reprod Biol Endocrinol (2010), 8:20; Kampfer et al. Life Sci. (2014) 97(2): 129-36; Bar-Josef et a. Reproductive Toxicology (2010), 30: 566-572; and Bar-Joseph et al. PLoS One (2011) 6: e23492].

Strategies aiming to preserve fertility in patients with different types of malignancies include in-vitro fertilization (IVF), embryo, oocyte and semen cryopreservation, cortical and whole ovary cryopreservation, ovarian transplantation, ovarian transposition, and GnRH agonist protection. To date, embryo and mature oocyte cryopreservation following IVF are the only techniques endorsed by the American Society of Reproductive Medicine.

Pigment epithelium-derived factor (PEDF) is a non-inhibitory member of the serine protease inhibitors (serpin) superfamily, which was first described as a neurotrophic factor, able to promote and support the growth of neuronal cells. It was later found that on top of having neurotrophic activity, PEDF has an anti-angiogenic, anti-inflammatory and anti-oxidative properties. To date, two distinct PEDF receptors were proposed: an 80 kDa PEDF putative receptor (PEDF-$R^N$; PNPLA2) involved in PEDF neuroprotecting, pro-survival functions; and a 60 kDa PEDF putative receptor (PEDF-$R^A$; Laminin receptor) involved in PEDF pro-apoptotic, anti-angiogenic activities [Manalo et al. Expert Opin Ther Pat (2011): 21, 121-130; and Yamagishi et al. Cell Tissue Res (2005) 320: 437-445]. Although originally discovered in culture media of retinal pigment epithelial cells, PEDF is widely expressed throughout the body: the nervous system, ovary, uterine, liver and plasma. Despite the significant expression of PEDF in the reproductive system, there is only limited data about its function in the ovary and uterus [Cheung et al., Endocrinology, 2006. 147(9): p. 4179-91; Chuderland et al. J Clin Endocrinol Metab (2013) 98: E258-266; and Chuderland et al. Mol Hum Reprod (2013) 19: 72-81; Pollina et al., Cell Cycle, 2008. 7(13): p. 2056-70; Palmieri et al. Exp Cell Res, 1999. 247(1): p. 142-7.]. Previous work has suggested using PEDF in the treatment of tumors mainly due to its anti-angiogenic effect [Manalo et al. Expert Opin Ther Pat (2011): 21, 121-130].

Additional Related Background Art:

U.S. Patent Publication Number US20130053312.
U.S. Patent Publication Number US20030216286.
U.S. Patent Publication Number US20070087967.
U.S. Patent Publication Number US20040071659.
U.S. Patent Publication Number US20090118191.
Nelius et al. [J Clin Oncol 31, 2013 (suppl 6; abstr 173)].
Choong et al. [The Liddy Shriver Sarcoma Initiative—PEDF: A Potential Therapeutic Agent for Osteosarcoma: sarcomahelpdotorg/research/osteosarcoma-pedfdothtml].
Ma and Waxman [Mol Cancer Ther. (2008) 7(12): 3670-3684].
Jia and Waxman [Cancer Lett. (2013) 330(2):241-9].

SUMMARY OF THE INVENTION

According to an aspect of some embodiments of the present invention there is provided a method of treating or preventing gonadal toxicity induced by an agent in a subject in need thereof, the method comprising administering to the subject a therapeutically effective amount of pigment epithelium-derived factor (PEDF), thereby treating or preventing the gonadal toxicity induced by the agent in the subject.

According to an aspect of some embodiments of the present invention there is provided a pigment epithelium-derived factor (PEDF) for use in the treatment or prevention of gonadal toxicity induced by an agent in a subject.

According to an aspect of some embodiments of the present invention there is provided a method of treating or preventing gonadal toxicity induced by an agent in a subject in need thereof, the method comprising:

(a) determining gonadal function in the subject; and (b) administering to the subject a therapeutically effective amount of pigment epithelium-derived factor (PEDF), thereby treating or preventing the gonadal toxicity induced by the agent in the subject.

According to some embodiments of the invention, the gonadal toxicity is selected from the group consisting of hypogonadism, reduced spermatogenesis, reduced ovulation, premature ovarian failure and sterility.

According to some embodiments of the invention, the gonadal toxicity comprises reduced ovulation.

According to some embodiments of the invention, the agent is selected from the group consisting of chemotherapy and radiotherapy.

According to some embodiments of the invention, the agent induces oxidative stress.

According to some embodiments of the invention, the subject is a female.

According to some embodiments of the invention, the female is at a reproductive-age.

According to some embodiments of the invention, the female has not been subjected to oocyte retrieval.

According to some embodiments of the invention, the subject is a male.

According to some embodiments of the invention, the male is at a reproductive-age.

According to some embodiments of the invention, the male has not been subjected to semen collection.

According to some embodiments of the invention, the subject is diagnosed with cancer.

According to some embodiments of the invention, the cancer is selected from the group consisting of testicular cancer, breast cancer, ovarian cancer, lymphoma and leukemia.

According to some embodiments of the invention, the chemotherapy treatment is administered in a maximum tolerated dose (MTD).

According to some embodiments of the invention, the chemotherapy is selected from the group consisting of mechlorethamine procarbazine cyclophosphamide, ifosfamide, busulfan, melphalan, chlorambucil, and chlormethine, doxorubicin, cisplatin and carboplatin.

According to some embodiments of the invention, the chemotherapy is selected from the group consisting of Alkylating agents, Procarbazine, Platinum analogs and anthracycline antibiotics.

According to some embodiments of the invention, the chemotherapy is selected from the group consisting of anthracycline antibiotics, alkylating agents, platinum-coordination complexes, epipodophyllotoxins and camptothecins.

According to some embodiments of the invention, the chemotherapy is doxorubicin.

According to some embodiments of the invention, the radiotherapy comprises pelvic irradiation.

According to some embodiments of the invention, the radiotherapy comprises total body irradiation (TBI).

According to some embodiments of the invention, the method further comprising administering the agent to the subject.

According to some embodiments of the invention, the administering the PEDF is effected concomitant with administering the agent.

According to some embodiments of the invention, the administering the PEDF is following administration of the agent.

According to an aspect of some embodiments of the present invention there is provided a method of treating cancer in a subject in need thereof, the method comprising administering to the subject a therapeutically effective amount of tamoxifen and a therapeutically effective amount of pigment epithelium-derived factor (PEDF), thereby treating the cancer.

According to an aspect of some embodiments of the present invention there is provided a tamoxifen and a pigment epithelium-derived factor (PEDF), for use in the treatment of cancer in a subject.

According to an aspect of some embodiments of the present invention there is provided a method of treating or preventing tamoxifen-induced uterine toxicity in a subject in need thereof, the method comprising administering to the subject a therapeutically effective amount of pigment epithelium-derived factor (PEDF), thereby treating or preventing the tamoxifen-induced uterine toxicity in the subject.

According to an aspect of some embodiments of the present invention there is provided a pigment epithelium-derived factor (PEDF) for use in the treatment or prevention of tamoxifen-induced uterine toxicity in a subject.

According to an aspect of some embodiments of the present invention there is provided an article of manufacture identified for use in treating cancer, comprising a packaging material packaging in separate containers tamoxifen and pigment epithelium-derived factor (PEDF).

According to an aspect of some embodiments of the present invention there is provided a pharmaceutical composition comprising as active ingredients a tamoxifen and pigment epithelium-derived factor (PEDF); and a pharmaceutically acceptable carrier or diluent.

According to some embodiments of the invention, the active ingredients are in a co-formulation.

According to some embodiments of the invention, the active ingredients are in separate formulations.

According to an aspect of some embodiments of the present invention there is provided a method of diagnosing tamoxifen-induced uterine toxicity in a subject, the method comprising determining the level of PEDF in a biological sample of the subject following treatment with tamoxifen, wherein a decrease below a predetermined threshold is indicative of the tamoxifen-induced uterine toxicity in the subject.

According to some embodiments of the invention, the method comprising determining the level of VEGF in the biological sample, wherein an increase above a predetermined threshold is indicative of the tamoxifen-induced uterine toxicity in the subject.

According to some embodiments of the invention, an increase in the ratio between VEGF and PEDF above a predetermined threshold in the biological sample is indicative of the tamoxifen-induced uterine toxicity in the subject.

According to some embodiments of the invention, the subject is a female.

According to some embodiments of the invention, the subject is at a reproductive-age.

According to some embodiments of the invention, the subject is at the pre-menopausal period.

According to some embodiments of the invention, the subject is at the post-menopausal period.

According to some embodiments of the invention, the subject is diagnosed with cancer.

According to some embodiments of the invention, the cancer is breast cancer.

According to some embodiments of the invention, the administering the PEDF is effected concomitant with administering the tamoxifen.

According to some embodiments of the invention, the administering the PEDF is following administration of the tamoxifen.

According to some embodiments of the invention, the administering the PEDF is effected by subcutaneous injection.

According to some embodiments of the invention, the administering the PEDF is effected by intravenous injection.

According to some embodiments of the invention, the administering the PEDF is effected at a dosage range of 0.02-0.4 mg/kg/day.

According to some embodiments of the invention, the administering the PEDF is effected at a dosage range of 0.162-0.32 mg/kg/day.

According to some embodiments of the invention, the PEDF is a PEDF peptide.

According to some embodiments of the invention, the gonadal function parameter is selected from the group consisting of hormonal evaluation, ultrasound evaluation and sperm analysis.

According to some embodiments of the invention, the hormonal evaluation is selected from the group consisting of LH, FSH, estradiol, AMH, testosterone, SHBG and progesterone.

According to some embodiments of the invention, the ultrasound evaluation is antral follicle count.

According to an aspect of some embodiments of the present invention there is provided a method of improving oocyte quality, the method comprising ex-vivo contacting an oocyte in a cell culture comprising the oocyte with an effective amount of pigment epithelium-derived factor (PEDF), thereby improving oocyte quality ex-vivo.

According to an aspect of some embodiments of the present invention there is provided a cell culture comprising an oocyte and an exogenously added pigment epithelium-derived factor (PEDF).

According to an aspect of some embodiments of the present invention there is provided an IVF grade medium for use in IVF comprising PEDF.

According to an aspect of some embodiments of the present invention there is provided a kit comprising:
(i) An IVF grade medium for use in IVF; and
(ii) PEDF.

According to some embodiments of the invention, the oocyte is maintained under conditions for in-vitro fertilization (IVF).

According to some embodiments of the invention, the contacting is effected before fertilization of the oocyte.

According to some embodiments of the invention, the contacting is effected following fertilization of the oocyte.

According to some embodiments of the invention, the contacting is effected concomitant with fertilization of the oocyte.

According to some embodiments of the invention, the contacting is effected following accumulation of oxidants in the culture above a predetermined threshold.

According to some embodiments of the invention, the oocyte is comprised in an ovary or an ovary fragment.

According to some embodiments of the invention, the oocyte for the IVF is comprised in an ovary or an ovary fragment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
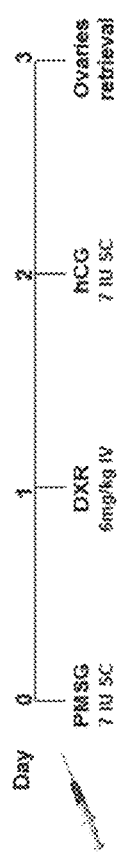
Figure 1B:
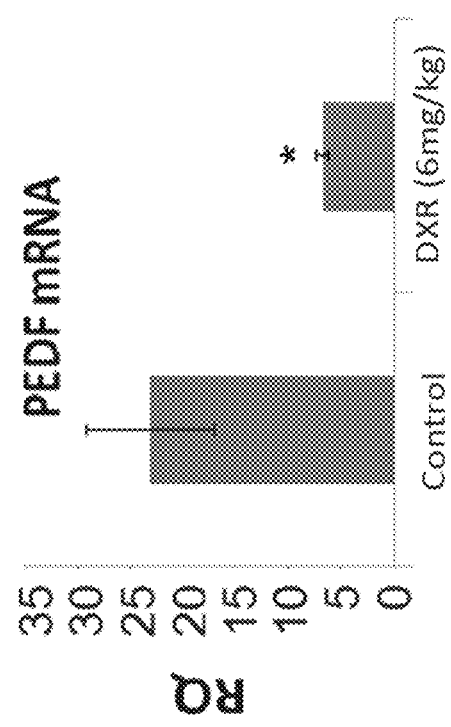

FIGS. 1A-B show that doxorubicin (DXR) reduces PEDF mRNA levels in mice ovaries. FIG. 1A is an illustration depicting the experimental setting: 7 weeks ICR female mice (n=5/group) were treated for superovulation with the standard pregnant mares' serum/human chorionic gonadotropin (PMSG/hCG) protocol [Ben-Aharon et al. Reproductive Biology and Endocrinology: RB&E (2010) 8: 20]. Twenty four hours post PMSG mice were administrated with DXR or saline (control). Ovaries were retrieved twenty four hours post hCG. FIG. 1B is a graph demonstrating PEDF mRNA levels in ovaries of control and DXR treated mice following the protocol described in FIG. 1A. Total RNA was extracted from the ovaries and changes in PEDF mRNA (relative quantification; RQ) level were measured by qPCR using specific primers for PEDF (SEQ ID NOs: 10-11); calibrated with HPRT (SEQ ID NOs: 6-7). (*$P<0.05$)— significantly different from control value.

Figure 2A:
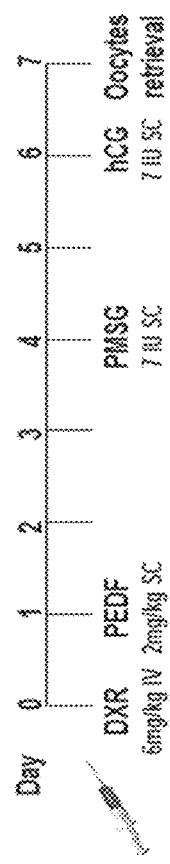
Figure 2B:
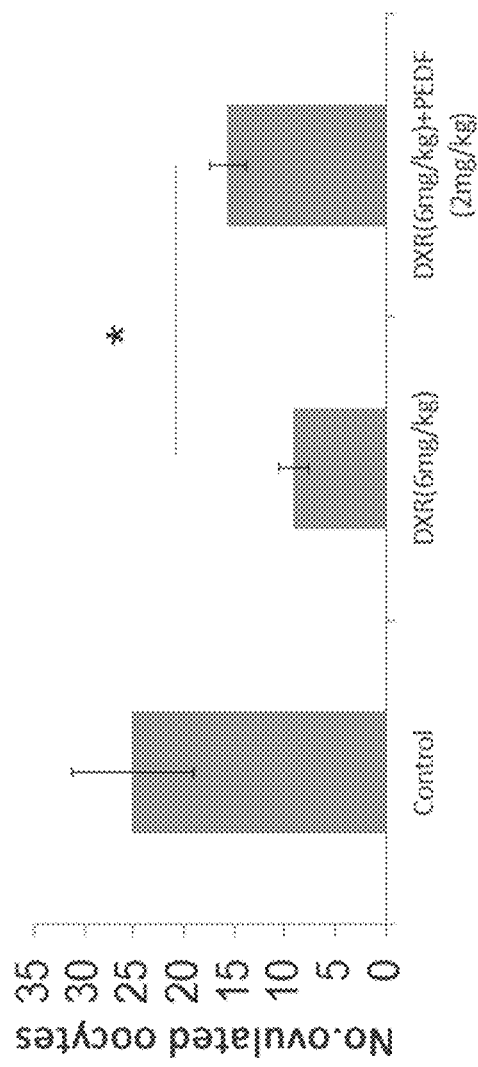

FIGS. 2A-B show that rPEDF improves ovulation under DXR treatment. FIG. 2A is an illustration depicting the experimental setting: 7 weeks ICR female mice (n=4/group) were treated with DXR or saline (control), at the day after mice were administrated with rPEDF or TRIS (control). On the fourth day of the experiment mice were induced for superovulation with the standard PMSG/hCG protocol [Ben-Aharon et al. Reproductive Biology and Endocrinology: RB&E (2010) 8: 20]. Mice were sacrificed 16-17 hours after hCG administration. FIG. 2B is a graph demonstrating the number of ovulated oocytes in control, DXR treated and DXR+rPEDF treated mice following the protocol described in FIG. 2A. Bars represent Mean±SEM, (*$P<0.05$)—significantly different from DXR value.

Figure 3A:
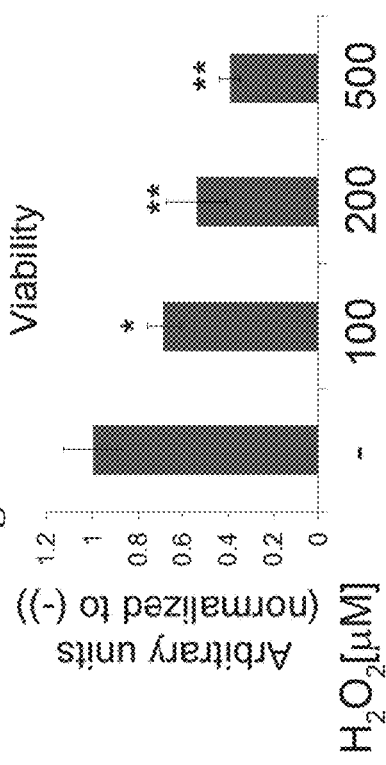
Figure 3B:
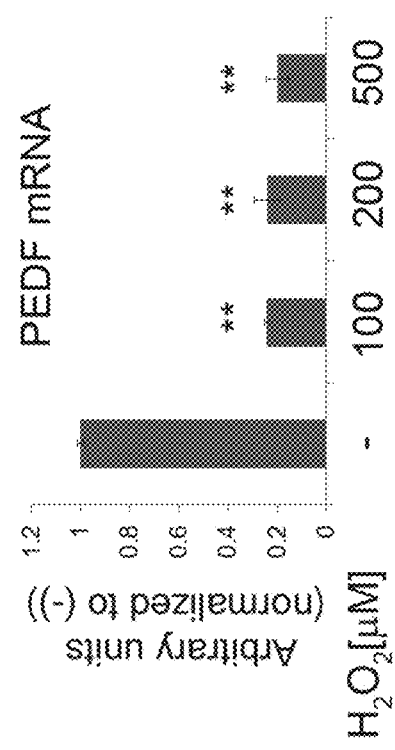

FIGS. 3A-B demonstrate $H_2O_2$ effects on granulosa cells' viability and PEDF mRNA. LH-15 cells were exposed to increasing doses of $H_2O_2$ (2% serum, 24 hours). FIG. 3A is a graph demonstrating cells viability as measured by MTT assay. Bars represent five independent experiments; the ratio between each treatment and the control is plotted as Mean±SDV, (*; $P<0.05$ and **; $p<0.01$)—Significantly different from control value. FIG. 3B is a graph demonstrating changes of PEDF mRNA levels as measured by qPCR analysis with specific primer for PEDF (SEQ ID NOs: 8-9); calibrated with HPRT (SEQ ID NOs: 6-7). Bars represent three independent experiments; the ratio between each treatment and the control is plotted as Mean±SDV, (*; P<0.05 and **; p<0.01)—Significantly different from control value.

Figure 4A:
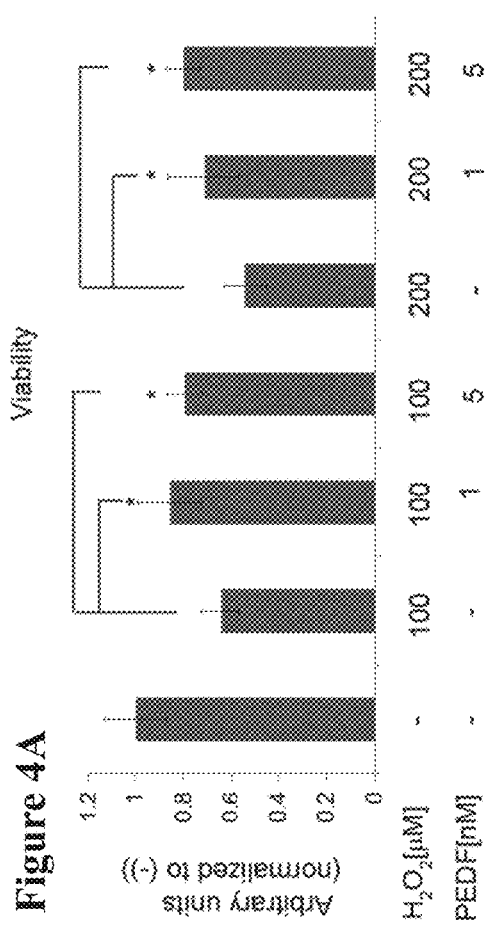
Figure 4C:
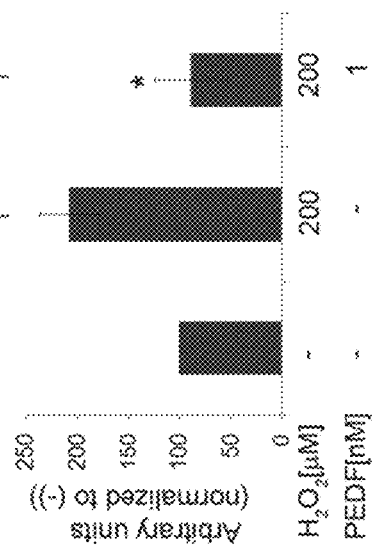
Figure 4B:

FIGS. 4A-C show that PEDF enhances LH-15 granulosa cells' viability under OS conditions. LH-15 cell line was exposed to increasing doses of $H_2O_2$ (2% serum, 24 hours) with or without rPEDF (1 nM and 5 nM). FIG. 4A is a graph demonstrating cells viability as measured by MTT assay. Bars represent three independent experiments; the ratio between each treatment and the control is plotted as Mean±SDV, (*; P<0.05 and **; p<0.01)—Significantly different from control value. FIG. 4B is a representative western blot photograph demonstrating BAX protein levels in the control and $H_2O_2$ treated cells using an anti BAX antibody. BAX protein level was calibrated with actin. FIG. 4C is a graph demonstrating densitometry analysis of BAX protein levels in the control and $H_2O_2$ treated cells as evaluated by western blot. The intensity of the bands was analyzed using the Image J software. Bars represent three independent experiments; the ratio between each treatment and the control is plotted as Mean±SDV, (*; P<0.05 and **; p<0.01)—Significantly different from control value.

FIGS. 5A-B demonstrate that rPEDF reverses the adverse effects of $H_2O_2$ on SOD-1 and GPX-1 mRNA levels in granulosa cells. LH-15 cells were exposed to $H_2O_2$ (2% serum, 24 hours) with or without rPEDF (1 nM). FIG. 5A is a graph demonstrating changes of SOD-1 mRNA levels and FIG. 5B is a graph demonstrating changes of GPX-1 mRNA levels as measured by qPCR analysis with specific primers for SOD-1 (SEQ ID NOs: 12-13) and GPX-1 (SEQ ID NOs: 14-15); calibrated with HPRT (SEQ ID NOs: 6-7). Bars represent three independent experiments; the ratio between each treatment and the control is plotted as Mean±SDV, (*; P<0.05 and **; p<0.01)—Significantly different from control value.

FIGS. 6A-C demonstrate the expression of the PEDF receptor, PNPLA2, in the ovary. FIG. 6A are representative immunohistochemistry photomicrographs of mouse ovarian sections labeled with anti PNPLA2 antibody (b, c) and a control of secondary antibody only (a). Bar represents 100 μM. FIG. 6B is an auto radiograph of representative PCR analyses (X35 cycles) demonstrating expression of PNPLA2 mRNA (lines a) in mouse ovaries (mouse) and LH-15 cells (rat). Control GAPDH (lines b). FIG. 6C is a representative Western blot photograph demonstrating PNPLA2 protein levels in mouse ovaries (mouse) and LH-15 cells (rat) using anti-PNPLA2 antibody.

Figure 7A:
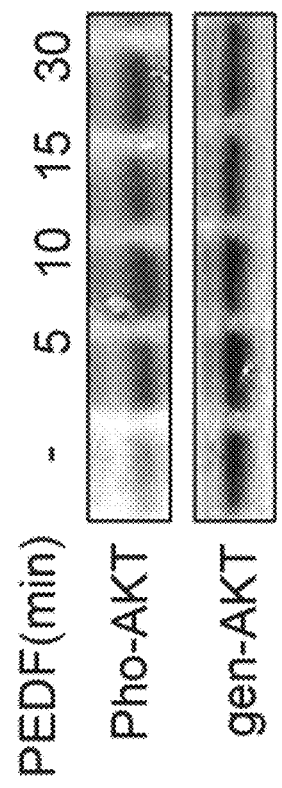
Figure 7B:
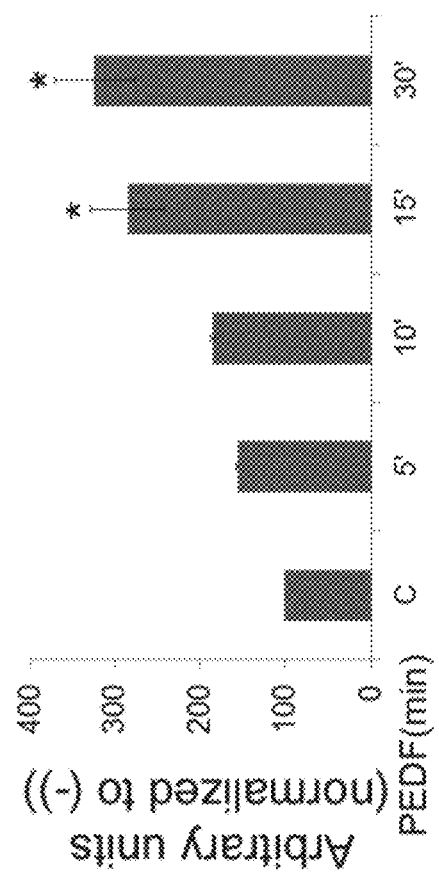

FIGS. 7A-B demonstrate that PEDF activates AKT signaling pathway in granulosa cells. LH-15 cells were serum starved (0.1%, 16 hours) and treated with rPEDF (1 nM) for several periods of time. FIG. 7A is a representative Western blot analysis photograph demonstrating phosphorylated AKT (Pho-AKT) and general AKT (gen-AKT) proteins levels in the control and rPEDF treated cells. FIG. 7B is a graph demonstrating densitometry analysis of the results shown in FIG. 7A. The intensity of the bands was analyzed using the Image J software. Bars represent three independent experiments; the ratio between Pho-AKT in each time point and the control is plotted as mean±SDV, (*; P<0.05)—Significantly different from control value.

Figure 8:
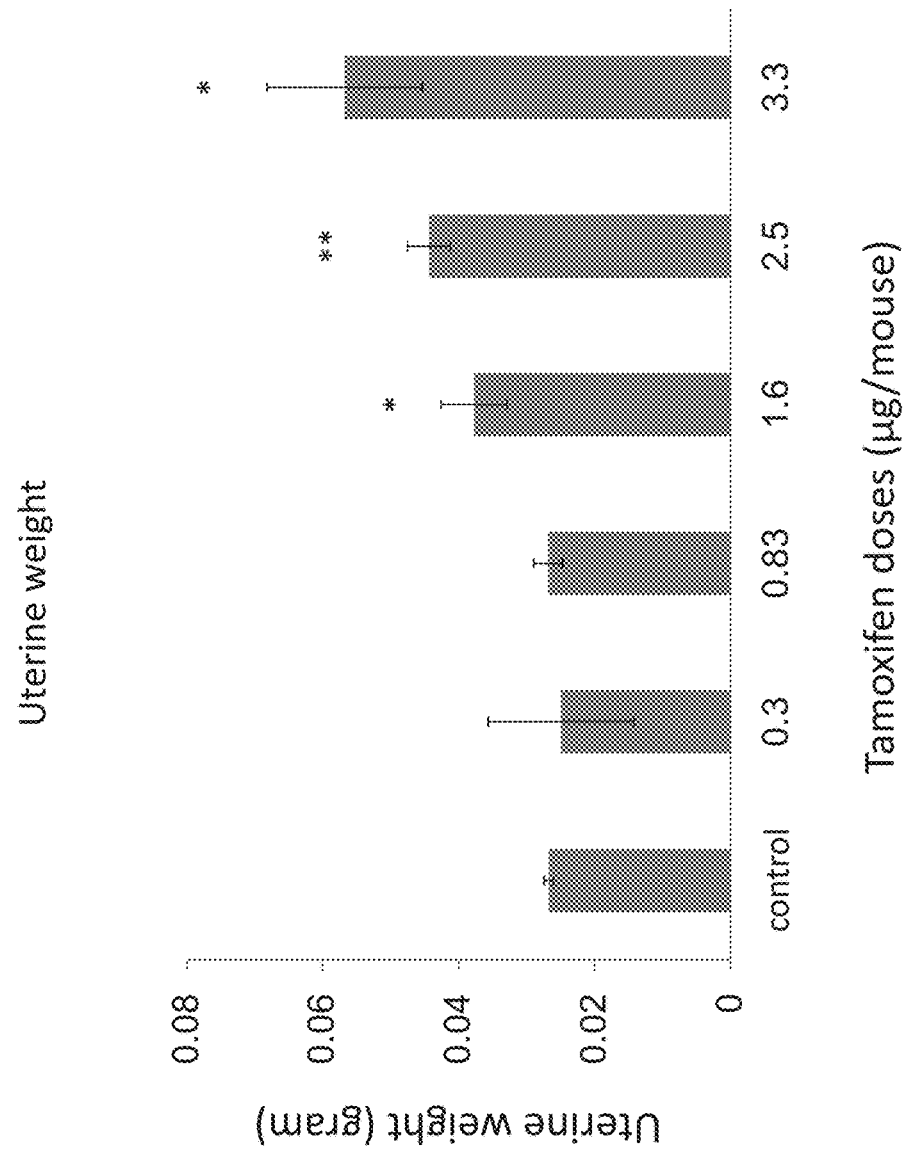

FIG. 8 is a bar graph showing uterine weight (in grams) of ovariectomized mice following 7 days treatment with tamoxifen demonstrating that sub-acute tamoxifen treatment increases uterine weight in a dose dependent manner. Bars represent Mean±SEM, (*P<0.05; **P<0.01)—significantly different from control value.

Figure 9B:
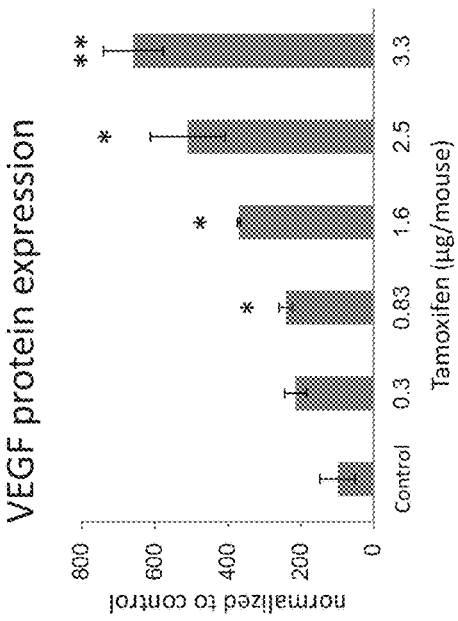
Figure 9D:
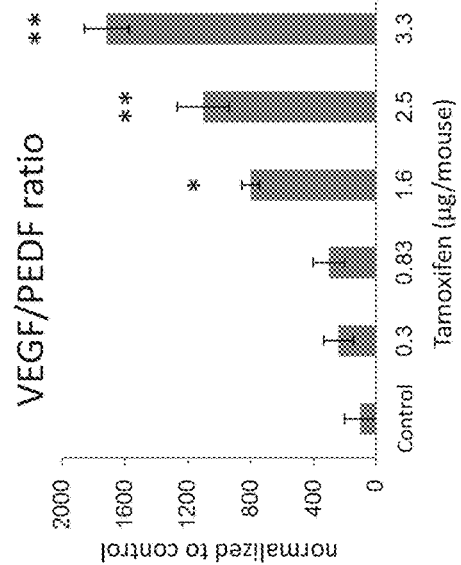
Figure 9A:
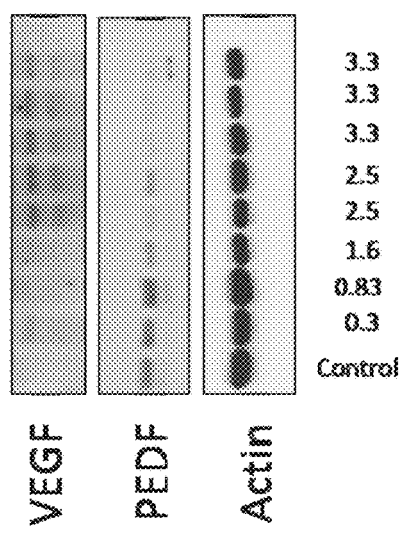
Figure 9C:
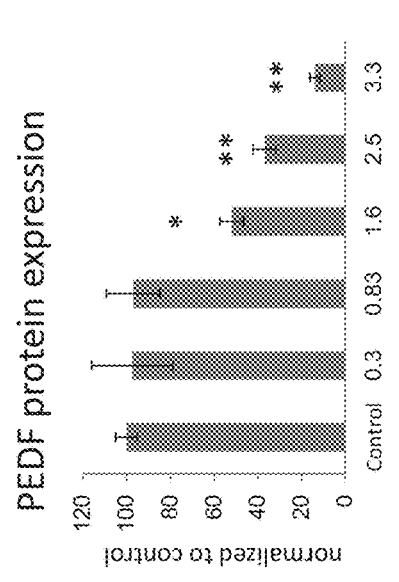

FIGS. 9A-D demonstrate that sub-acute tamoxifen treatment increases VEGF levels while decreasing PEFD levels in uteri of ovariectomized mice. Ovariectomized mice were administered with tamoxifen for 7 days. FIG. 9A are representative Western blot analysis photographs showing VEGF and PEDF protein levels. FIGS. 9B-D are bar graphs showing densitometry analysis of the VEGF protein levels (FIG. 9B), PEDF protein levels (FIG. 9C) and VEGF/PEDF ratio (FIG. 9D) as evaluated by western blot. The intensity of the bands was analyzed using the Image J software and normalized to actin as loading control. Bars represent the ratio between each treatment and the control plotted as mean±SEM, n=3/4 mice per group, (*P<0.05; **P<0.01)—significantly different from control value.

Figure 10:
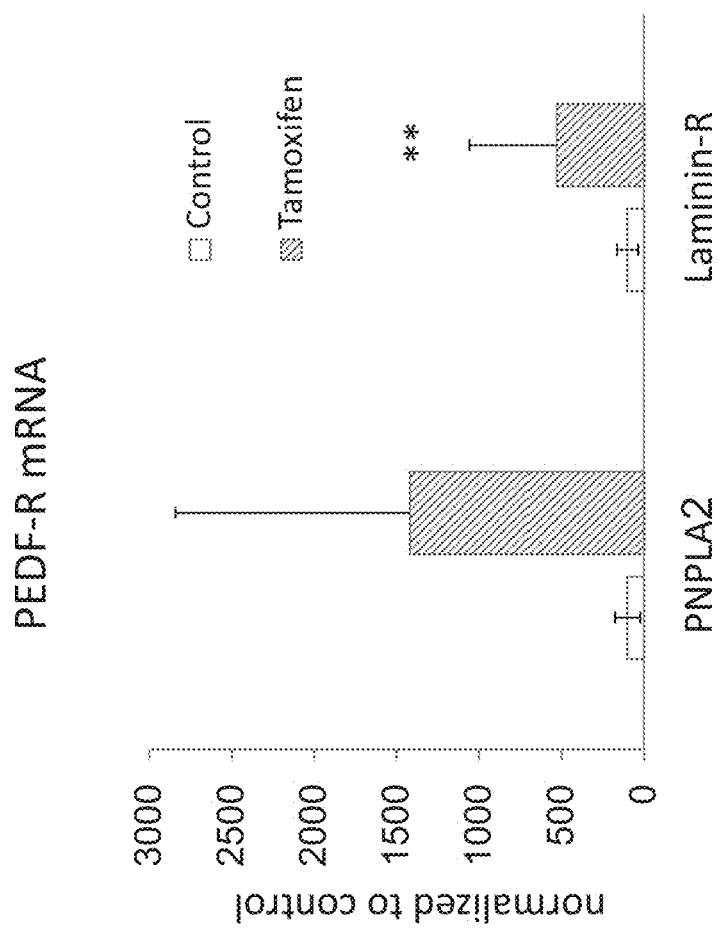

FIG. 10 demonstrates the effect of sub-acute tamoxifen treatment on the mRNA levels of the PEDF receptors PNPLA2 and Laminin-R in uteri of ovariectomized mice as measured by qPCR analysis with specific primer for PNPLA2 (SEQ ID NOs: 16-17) and Laminin-R (SEQ ID NOs: 18-19); calibrated with HPRT (SEQ ID NOs: 6-7). Bars represent the ratio between treatment and the control plotted as mean±SEM, n=3/4 mice per group**P<0.01)—significantly different from control value.

Figure 11:
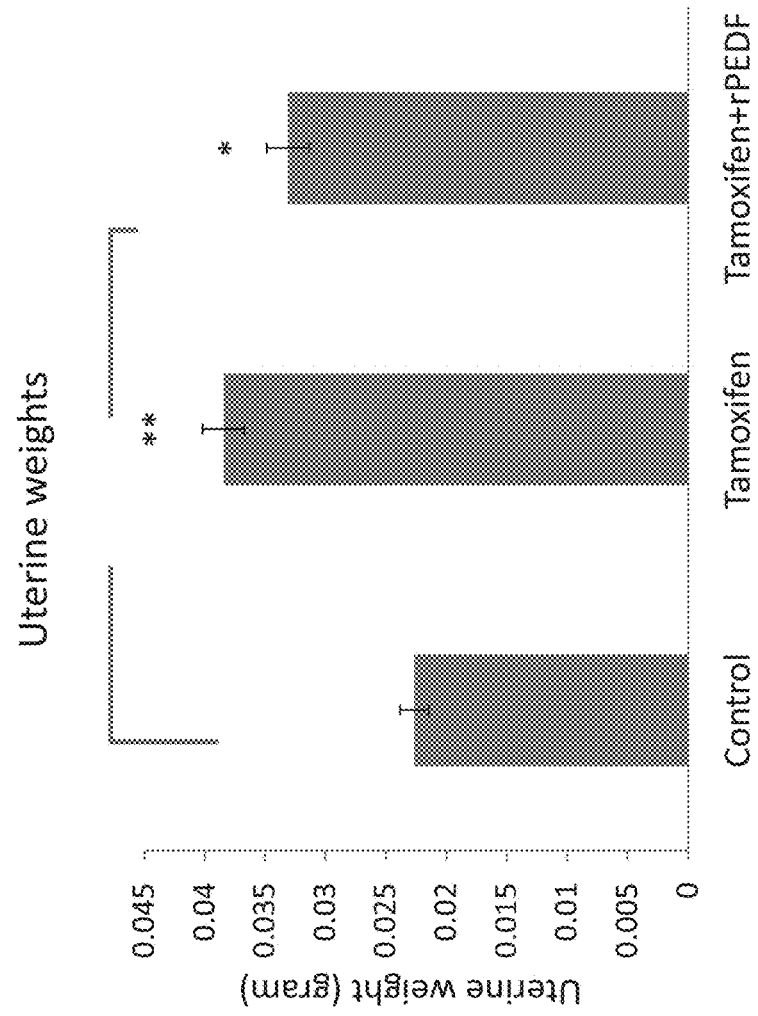

FIG. 11 is a bar graph showing uterine weight of ovariectomized mice following 7 days treatment with solvent only (control group), tamoxifen alone or in combination with PEDF and demonstrating that treatment with rPEDF decreases the adverse effect of sub-acute tamoxifen treatment on uterine weight. Ovariectomized mice were administered with solvent only (control group), tamoxifen or with a combination of tamoxifen and rPEDF for 7 days. Bars represent the ratio between each treatment and the control (tamoxifen alone) plotted as mean±SEM, Control n=13; tamoxifen n=22; tamoxifen+rPEDF n=16, (*P<0.05; **P<0.01)—significantly different from control value.

FIGS. 12A-B demonstrate that treatment with rPEDF decreases the adverse effect of sub-acute tamoxifen treatment on VEGF protein levels in uteri of ovariectomized mice. Ovariectomized mice were administered with solvent only (control group), tamoxifen or with a combination of tamoxifen and rPEDF for 7 days. FIG. 12A is a representative Western blot photograph showing VEGF protein levels. FIG. 12B is a bar graph showing VEGF protein levels as evaluated by densitometry analysis of the Western blot analysis results shown in FIG. 12A. The intensity of the bands was analyzed using the Image J software and normalized to actin as loading control. Bars represent the ratio between each treatment and the control plotted as mean±SEM, Control n=13; tamoxifen n=22; tamoxifen+rPEDF n=16. (**P<0.01)—significantly different from control value.

Figure 13A:
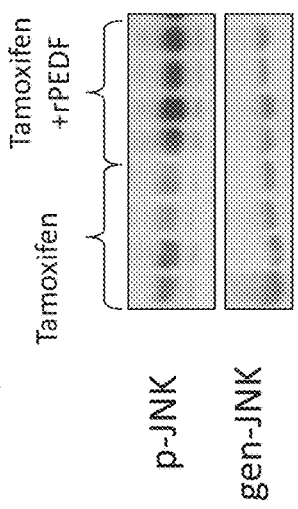
Figure 13B:
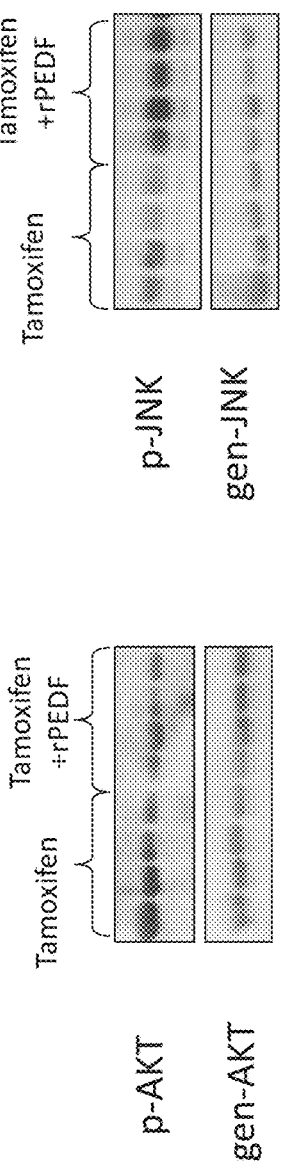

FIGS. 13A-B demonstrate that PEDF downregulates activation of AKT signaling pathway in uteri of ovariectomized mice following sub-acute tamoxifen treatment. Ovariectomized mice were administered with tamoxifen alone or with a combination of tamoxifen and rPEDF for 7 days. FIG. 13A is a representative Western blot analysis photograph demonstrating phosphorylated AKT (p-AKT) and general AKT (gen-AKT) proteins levels in the tamoxifen alone (control) and tamoxifen plus rPEDF treated mice. FIG. 13B is a bar graph demonstrating p-AKT levels as evaluated densitometry analysis of the Western blot analysis results shown in FIG. 13A. The intensity of the bands was analyzed using the Image J software and normalized to gen-AKT. Bars represent the ratio between p-AKT in each treatment and the control plotted as mean±SEM, n=4 mice per group (**; P<0.01)—Significantly different from control value.

Figure 14A:
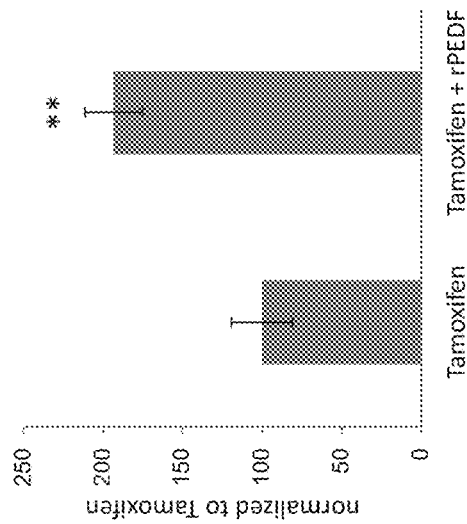
Figure 14B:
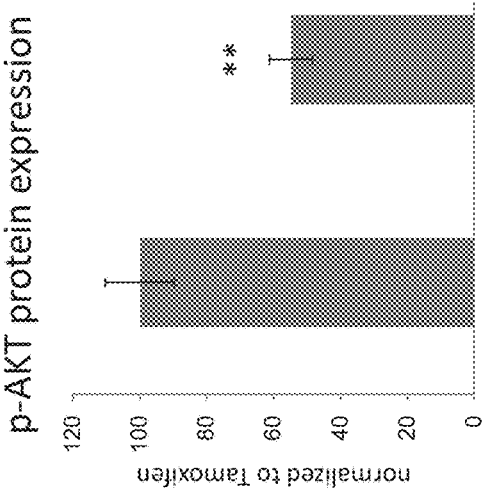

FIGS. 14A-B demonstrate that PEDF upregulates activation of JNK signaling pathway in uteri of ovariectomized mice following sub-acute tamoxifen treatment. Ovariectomized mice were administered with tamoxifen alone or with a combination of tamoxifen and rPEDF for 7 days. FIG. 14A is a representative Western blot photograph demonstrating phosphorylated JNL (p-JNK) and general JNK (gen-JNK) proteins levels in the tamoxifen alone (control) and tamoxifen plus rPEDF treated mice. FIG. 14B is a bar graph demonstrating p-JNK levels as evaluated by densitometry analysis of the Western blot analysis results shown in FIG. 14A. The intensity of the bands was analyzed using the Image J software and normalized to gen-JNK. Bars represent the ratio between p-JNK in each treatment and the control plotted as mean±SEM, n=4 mice per group (**; P<0.01)— Significantly different from control value.

Figure 15:
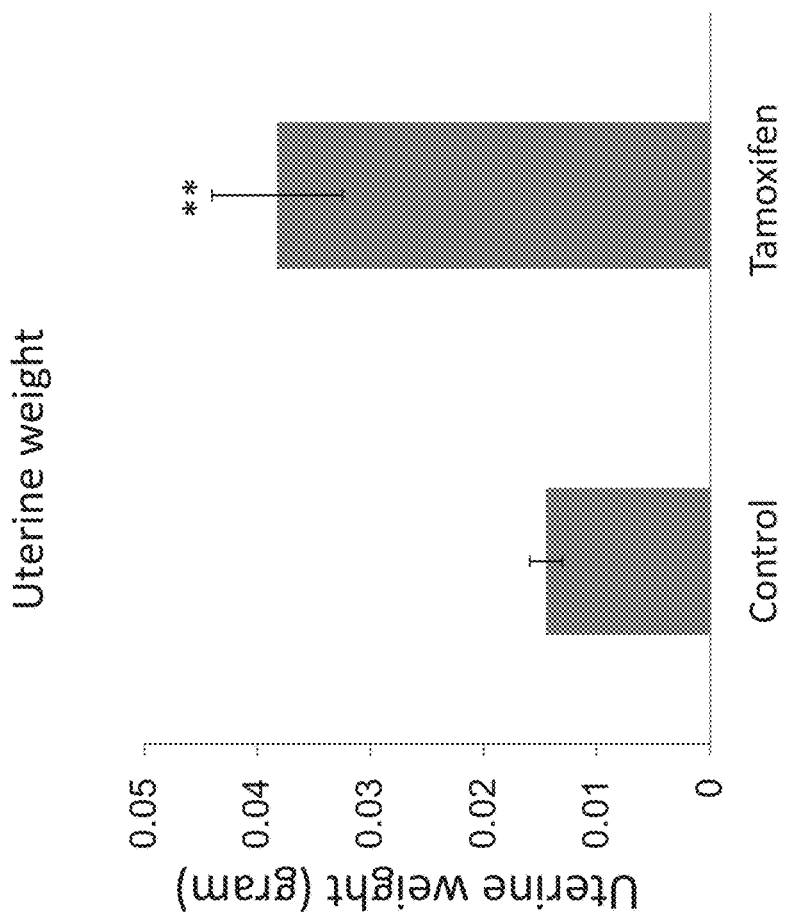

FIG. 15 is a bar graph showing uterine weight (in grams) of ovariectomized mice following prolonged treatment with tamoxifen (2.5 μg per mouse/5 days per week for one month) demonstrating that prolonged tamoxifen treatment significantly increases uterine weight. Bars represent the ratio between each treatment and the control plotted as mean±SEM, n=6/7 mice per group (**P<0.01)—significantly different from control value.

Figure 16A:
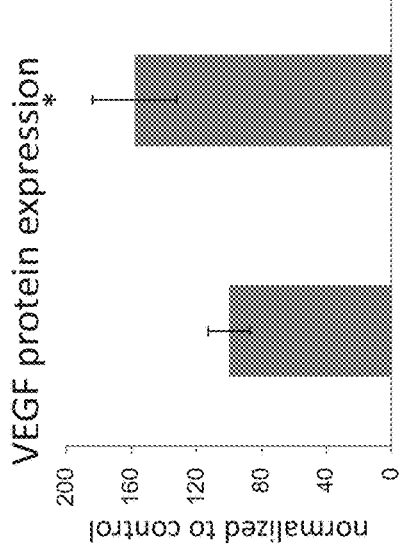
Figure 16C:
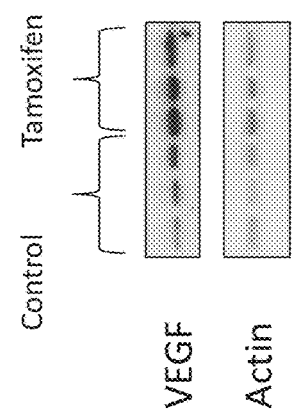
Figure 16B:
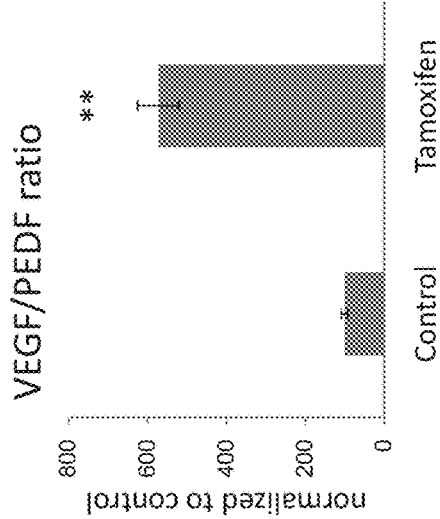
Figure 16D:
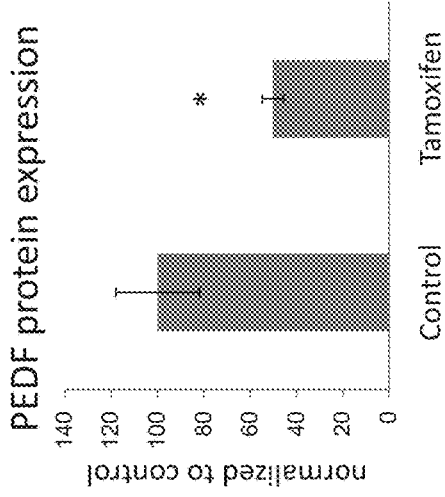

FIGS. 16A-D demonstrate that prolonged tamoxifen treatment increases VEGF levels while decreasing PEFD levels in uteri of ovariectomized mice. Ovariectomized mice were administered with tamoxifen for 5 days per week for one month. FIG. 16A is a representative Western blot photograph showing VEGF protein levels. FIGS. 16B-D are bar graphs showing densitometry analysis of VEGF protein levels (FIG. 16B), PEFD protein levels (FIG. 16C) and VEGF/PEFD ratio (FIG. 16D) as evaluated by western blot. The intensity of the bands was analyzed using the Image J software and normalized to actin as loading control. Bars represent the ratio between each treatment and the control plotted as mean±SEM, n=6/7 mice per group (*P<0.05; **P<0.01)—significantly different from control value.

Figure 17:
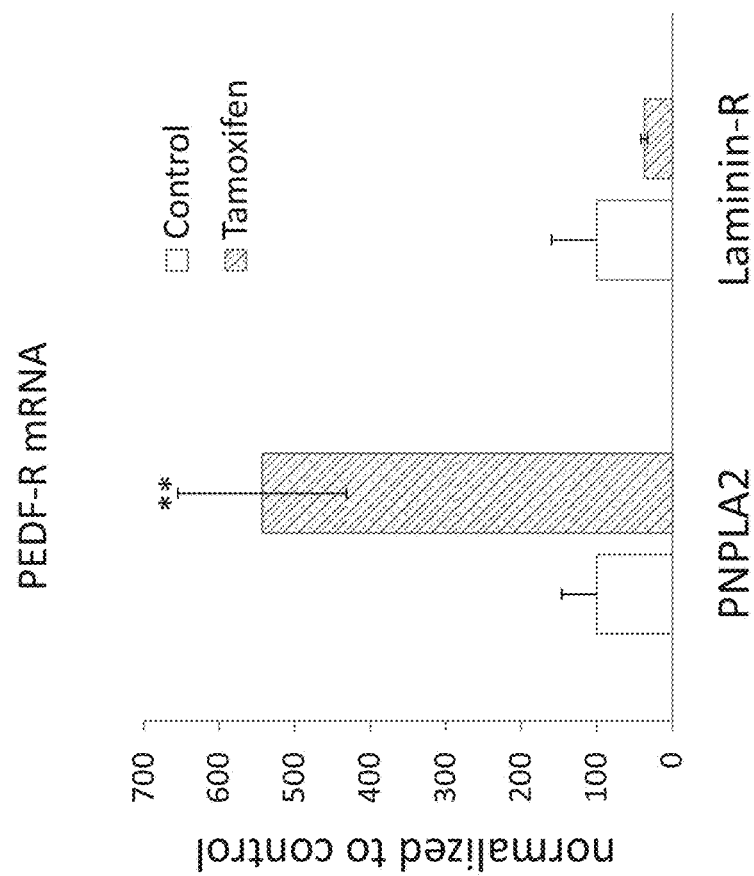

FIG. 17 demonstrates the effect of prolonged tamoxifen treatment on the mRNA levels of the PEDF receptors PNPLA2 and Laminin-R in uteri of ovariectomized mice, as measured by qPCR analysis with specific primer for PNPLA2 (SEQ ID NOs: 16-17) and Laminin-R (SEQ ID NOs: 18-19); calibrated with HPRT (SEQ ID NOs: 6-7). Bars represent the ratio between treatment and the control plotted as mean±SEM, n=6/7 mice per group, **P<0.01)—significantly different from control value.

Figure 18:
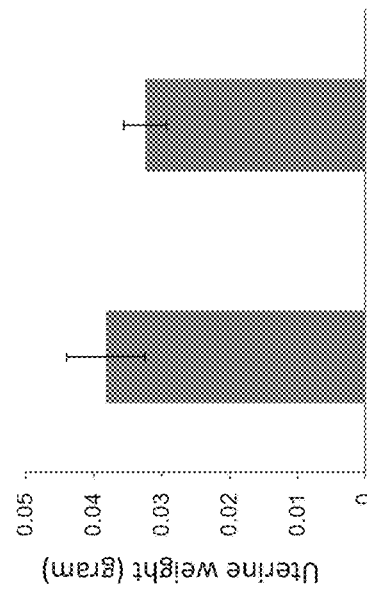

FIG. 18 is a bar graph showing uterine weight (in grams) of ovariectomized mice following prolonged treatment with tamoxifen alone or in combination with PEDF and demonstrating that treatment with rPEDF decreases the adverse effect of sub-acute tamoxifen treatment on uterine weight. Ovariectomized mice were administered with tamoxifen 5 days per week for one month or with a combination of tamoxifen and rPEDF. Bars represent Mean±SEM, n=6 mice per group.

Figure 19B:
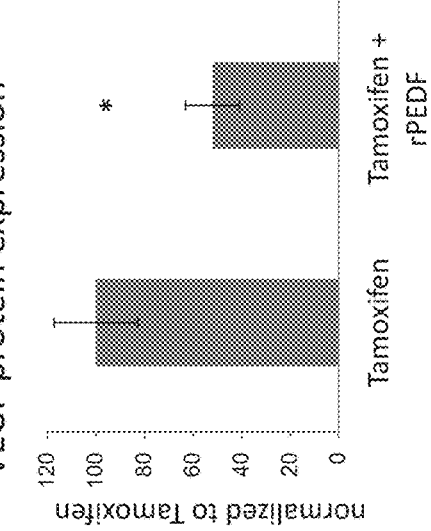
Figure 19A:
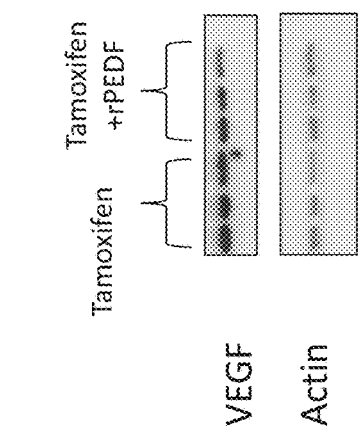

FIGS. 19A-B demonstrate that treatment with rPEDF decreases the adverse effect of prolonged tamoxifen treatment on VEGF protein levels in uteri of ovariectomized mice. Ovariectomized mice were administered with tamoxifen 5 days per week for one month or with a combination of tamoxifen and rPEDF. FIG. 19A is a representative Western blot photograph showing VEGF protein levels. FIG. 19B is a bar graph showing VEGF protein levels as evaluated by densitometry analysis of the Western blot analysis results shown in FIG. 19A. The intensity of the bands was analyzed using the Image J software and normalized to actin as loading control. Bars represent the ratio between each treatment and the control (tamoxifen alone) plotted as mean±SEM, n=6 mice per group (*P<0.05)— significantly different from control value.

Figure 20:
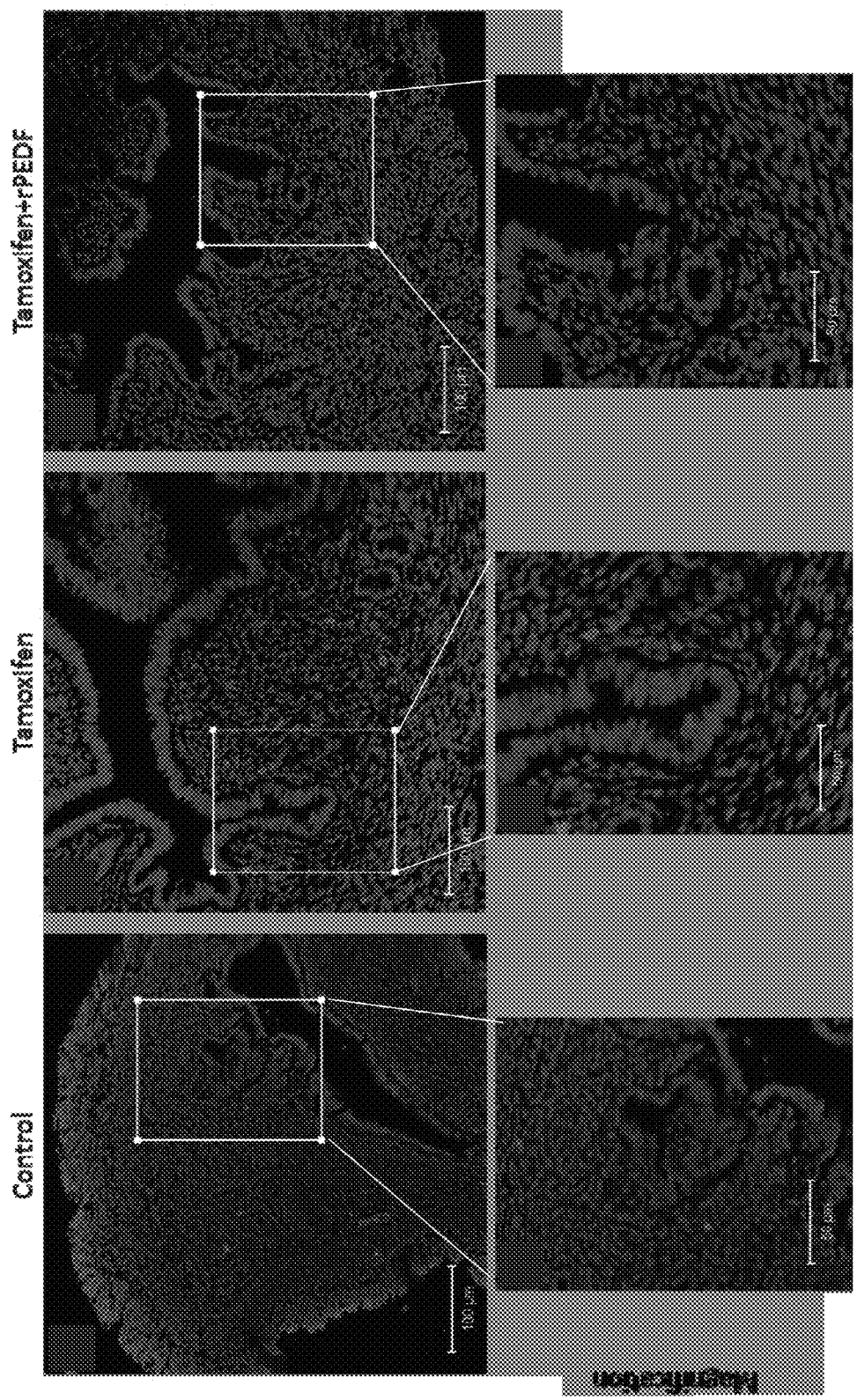

FIG. 20 shows representative immunohistochemical photomicrographs demonstrating CD34 staining (red) in uteri of control, prolonged tamoxifen and prolonged tamoxifen+ rPEDF treated mice. The lower panel shows magnifications of the selected areas marked with white. Counterstaining was effected with Hoechst 32242 (blue).

Figure 21A:
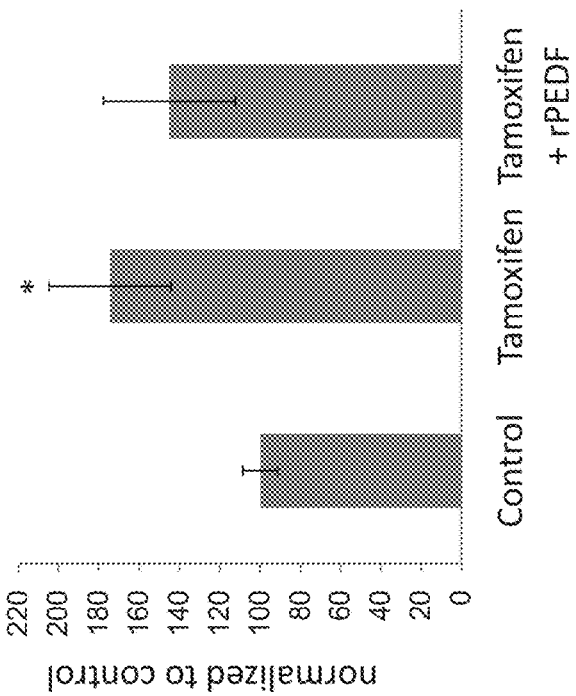
Figure 21B:
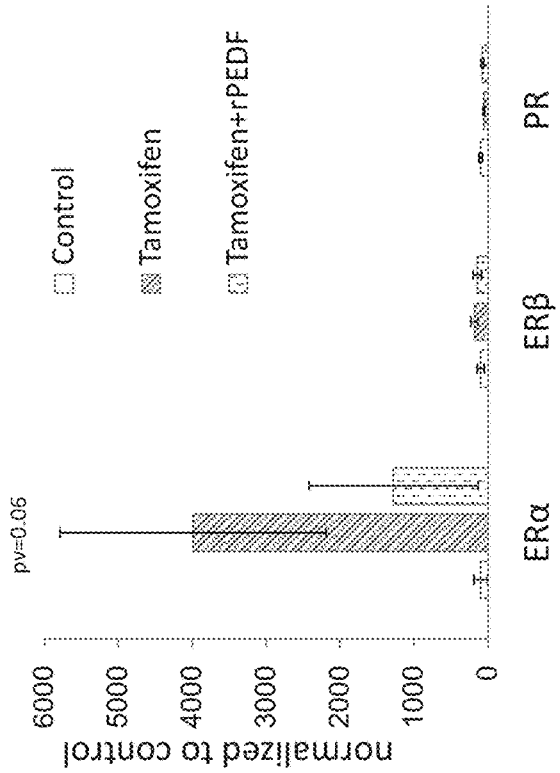

FIGS. 21A-B demonstrate the effect of sub-acute tamoxifen treatment with and without rPEDF on the expression of the hormonal receptors estrogen receptor α (ERα), estrogen receptor β (ERβ) and progesterone receptor (PR), in uteri of ovariectomized mice. FIG. 21A shows mRNA levels of ERα, ERβ and PR as measured by qPCR analysis with specific primers for ERα (SEQ ID NOs: 20-21), ERfβ (SEQ ID NOs: 22-23) and PR (SEQ ID NOs: 24-25); calibrated with HPRT (SEQ ID NOs: 6-7). FIG. 21B shows densitometry analysis of ERα protein levels as evaluated by western blot. The intensity of the bands was analyzed using the Image J software and normalized to actin as loading control. Bars represent the ratio between each treatment and the control plotted as mean±SEM, n=4 mice per group.

Figure 22B:
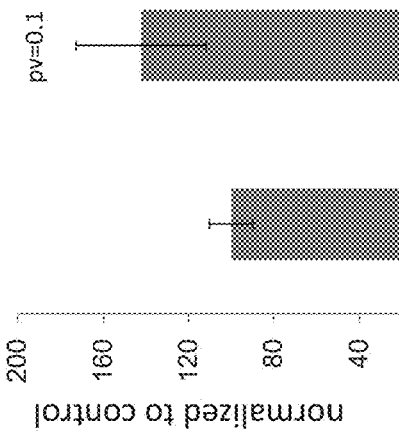
Figure 22A:
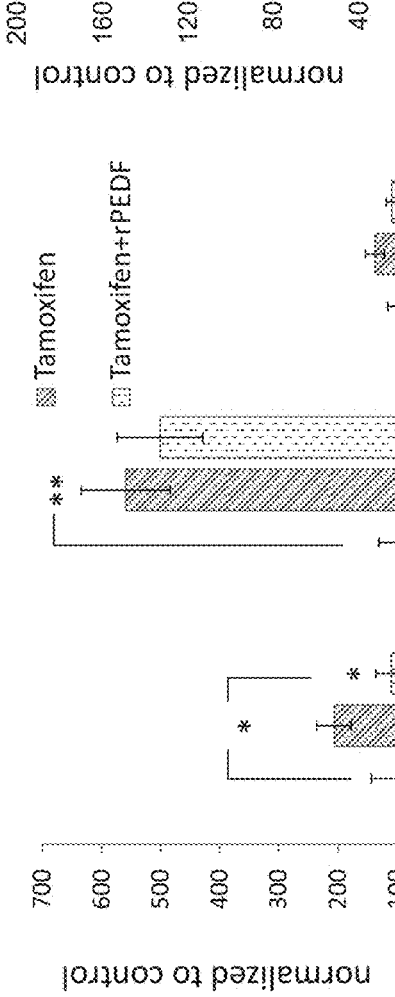

FIGS. 22A-B demonstrate the effect of prolonged tamoxifen treatment with and without rPEDF on the expression of the hormonal receptors estrogen receptor α (ERα), estrogen receptor β (ERβ) and progesterone receptor (PR), in uteri of ovariectomized mice. FIG. 22A shows mRNA levels of ERα, ERβ and PR as measured by qPCR analysis with specific primers for ERα (SEQ ID NOs: 20-21), ERβ (SEQ ID NOs: 22-25) and PR (SEQ ID NOs: 24-25); calibrated with HPRT (SEQ ID NOs: 24-25). FIG. 22B shows densitometry analysis of ERα protein levels as evaluated by western blot. The intensity of the bands was analyzed using the Image J software and normalized to actin as loading control. Bars represent the ratio between each treatment and the control plotted as mean±SEM, n=6 mice per group, (*P<0.05; **P<0.01)—significantly different from control value.

DESCRIPTION OF SPECIFIC EMBODIMENTS OF THE INVENTION

The present invention, in some embodiments thereof, relates to methods of using PEDF for the treatment and prevention of agent-induced gonadal or uterine toxicity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The treatment for most cancer types involves cytotoxic treatments such as chemotherapy and radiotherapy that may partially or definitively induce gonadal or uterine toxicity.

PEDF is a multifunctional factor endowed with neurotrophic, anti-angiogenic, anti-inflammatory and anti-oxidative properties which is ubiquitously expressed in the body. Despite significant expression in the reproductive system, there is only limited data about PEDF function in the ovary and uterus. Previous work has suggested using PEDF in the treatment of tumors due to its direct anti-tumorigenic and anti-angiogenic effect. However, the role of PEDF in protecting the gonads from the destructive effects of chemotherapy and radiotherapy has never been disclosed.

Whilst reducing the present invention to practice, the present inventors have now uncovered that administration of PEDF can prevent gonadal or uterine toxicity induced by toxic agents such as chemotherapy treatment and suggest its use in the treatment or prevention of agent-induced gonadal toxicity and tamoxifen-induced uterine toxicity.

As is illustrated herein below (Example 1 and FIGS. 1A-B and 2A-B), the present inventors have found that the chemotherapeutic agent DXR reduced PEDF mRNA expression in ovaries of DXR-treated mice and that administration of rPEDF after DXR treatment significantly improved the number of the ovulated oocytes in DXR-treated mice. Furthermore, the present inventors have found that oxidative stress induction (e.g., $H_2O_2$) had a negative dose dependent effect on PEDF mRNA expression in LH-15 rat granulosa cells and administration of rPEDF significantly attenuated the rate of oxidative stress-related to $H_2O_2$ in general i.e., oxidative stress-induced apoptosis, decreased the elevated oxidative stress-induced expression of the pro-apoptotic protein BAX and increased SOD-1 and GPX-1 levels (Example 2 and FIGS. 4A-B, 5A-B and 6A-B). As further shown in Example 3 and FIGS. 6A-C and 7A-B, the present inventors have demonstrated that granulosa cells, theca cells and oocytes express the PEDF pro-survival receptor, PNPLA2; and once stimulated by rPEDF, LH-15 granulosa cells exhibit phosphorylation of AKT indicative of activation of pro-survival cell signaling.

Consequently these findings show that administration of PEDF can prevent gonadal toxicity induced by chemotherapy treatment such as DXR and suggest its use in the treatment or prevention of agent-induced gonadal toxicity.

As is further illustrated herein below (Example 4 and FIGS. 8, 9A-B, 15, 16A-C, 18, 19A-B, 20), the present inventors have shown that both sub-acute and prolonged tamoxifen treatment increased uterine weight, upregulated VEGF protein levels, decreased PEDF protein levels and increased the ratio between VEGF and PEDF protein levels in uteri of ovariectomized mice. The present inventors have shown that combined administration of tamoxifen and rPEDF significantly attenuated the adverse effects induced by tamoxifen on uterine weight and VEGF expression. Furthermore, as shown in Example 4 and FIGS. 10, 13A-B, 14A-B, 17, 21A-B and 22A-B) tamoxifen treatment up-regulated the expression of the PEDF pro-survival receptor, PNPLA2; and combined treatment with tamoxifen and rPEDF induced increase in the phosphorylation of the pro-apoptotic signaling molecule, JNK, a decrease in the phosphorylation of the pro-survival signaling molecule, AKT and a specific decrease in ERα uterine expression.

Consequently, these findings show that administration of PEDF can prevent the deleterious effects on the uterus induced by tamoxifen treatment and suggest its use in the treatment or prevention of tamoxifen-induced uterine toxicity.

Thus, according to an aspect of the present invention there is provided a method of treating or preventing gonadal toxicity induced by an agent in a subject in need thereof, the method comprising administering to the subject a therapeutically effective amount of pigment epithelium-derived factor (PEDF), thereby treating or preventing the gonadal toxicity induced by the agent in the subject.

According to another aspect of the present invention there is provided a method of treating or preventing gonadal toxicity induced by an agent in a subject in need thereof, the method comprising:

(a) determining gonadal function in a subject; and (b) administering to the subject a therapeutically effective amount of pigment epithelium-derived factor (PEDF), thereby treating or preventing the gonadal toxicity induced by the agent in said subject.

According to yet another aspect of the present invention there is provided a pigment epithelium-derived factor (PEDF) for use in the treatment or prevention of gonadal toxicity induced by an agent in a subject.

As used herein, "Pigment epithelium-derived factor (PEDF)", also known as serpin F1, EPC-1, cell proliferation inducing gene 35 protein and PIG35 and interchangeably referred to rPEDF, refers to a polynucleotide and an expression product e.g. protein of the SERPINF1 gene. According to a specific embodiment, the PEDF protein refers to the human protein, such as provided in the following GenBank Numbers NM_002615.4 (SEQ ID NO: 1), M76979 (SEQ ID NO: 26), or NP_002606.3 (SEQ ID NO: 27). The PEDF of the present invention is functional in at least one of but in some embodiments all of preventing gonadal toxicity, preventing uterine toxicity, interfering with VEGF signaling, inducing pro-survival, anti-angiogenic, anti-inflammatory, anti-tumorigenic and/or anti-oxidative signals. Methods of qualifying PEDF for use in accordance with the present invention are well known in the art (some are described in the Examples section e.g., effect on uterine weight of tamoxifen treated animals, effect on VEGF uterine expression of tamoxifen treated animals, effect on ERa uterine expression of tamoxifen treated animals, effect on the number of ovulated oocytes of DXR treated animals, effect of oxidative stress on apoptosis and expression of apoptosis related proteins of granulose cells, etc.).

The term PEDF refers to non-modified and modified PEDF. According to a specific embodiment, the PEDF is a phosphorylated PEDF. PEDF is phosphorylated on 3 distinct sites Ser24 and Ser114 by casein kinase 2 (CK2) and on Ser227 by protein kinase A (PKA). Specifically, contemplated is the use of the triple phosphorylated PEDF. U.S. Publication No. US20080274967 teaches phosphorylation of PEDF using CK2 and PKA and is fully incorporated herein.

The term PEDF also refers to PEDF peptide fragments. The present invention also contemplates the use of PEDF peptides which retain the biological activity of full-length PEDF, i.e., treatment or prevention of gonadal toxicity induced by an agent or treatment or prevention tamoxifen-induced uterine toxicity such as those disclosed for example in U.S. Publication Nos. US20090069241 and US20120245097; and PCT Publication Nos. WO2014023007 and WO2013184986, each of which is herein incorporated by reference in its entirety.

PEDF can be purified as described in Yanagishe et al. 2006 J. Endocrinol. Metab. 91:2447-2450. Alternatively, PEDF is commercially available from Biovendor Inc.

As used herein a "PEDF Receptor", "PEDFR" or "PEDF-R" refers to a cell surface molecule which binds PEDF and initiates signal transduction such as via the FasL; CD95, Ras; Raf; Mekk1; Mek; Erk; JNK; IP3; Akt; IKK; NF-kappa-B; PLA2; and PPAR-γ pathways.

According to a specific embodiment, the PEDF receptor is an 80 kDa PEDF receptor, referred to as PEFD-$R^N$; PNPLA2, involved in PEDF neuroprotecting, pro-survival functions.

According to an additional or alternative embodiment, the PEDF receptor is a 60 kDa PEDF receptor, referred to as PEDF-$R^A$; laminin receptor, involved in PEDF pro-apoptotic, anti-angiogenic activities.

According to a specific embodiment, PEDF exerts its function through the 80 kDa PEDF receptor denoted PEFD-$R^N$ or PNPLA2.

As used herein, the term "agent induced gonadal toxicity" refers to a temporary or permanent insult to the reproductive organs which include the ovaries or the testes that is induced by intake of an exogenous agent as described hereinbelow. According to specific embodiments, the insult to the reproductive organs results in a decrease in gonadal function in comparison to normal gonadal function for subjects of the same age as the treated subject and having normal gonadal function such as according to national health agencies. According to a specific embodiment, the decrease is in at least 10%, 20%, 30%, 40% or even higher say, 50%, 60%, 70%, 80%, 90% or more than 100% as compared to prior to treatment. Decreased gonadal function may be evaluated by any method known in the art such as, but not limited to hormonal evaluation, ultrasound evaluation and/or semen analysis; as further detailed hereinbelow.

According to specific embodiments, the gonadal toxicity affects the reproduction related functions of the gonads.

According an additional or alternative embodiment, the gonadal toxicity is accompanied by cell death and/or impairment of cellular functions in the gonads.

According an additional or alternative embodiment, the gonadal toxicity is accompanied by impaired hormone production (e.g. estrogen, progesterone, and testosterone).

Non-limiting manifestations of gonadal toxicity include sterility, hypogonadism, reduced ovulation, premature ovarian failure, premature menopause, epithelial (mesothelial) and tubular hyperplasia, oocyte destruction, apoptosis of granulosa cells, arrest of follicular development up to follicular atresia, follicular and interstitial atrophy, supraovulation, follicular luteinisation, follicular cysts, reduction/absence of corpora lutea, increased/persistence of corpora lutea, vacuolar degeneration of corpora lutea, sertoliform tubular hyperplasia, interstitial gland hypertrophyhyperplasia atrophy, disturbance of estrous cycle, mesovarial smooth muscle hyperplasia, reduced spermatogenesis, reduced sperm output or reduced testosterone secretion from the testis, interference with the transport of sperm through the duct system, impaired sperm quality, germ cell degeneration, disorganization, exfoliation and/or depletion, reduced fluid secretion in the testis and tubular contraction, and Leydig cell hyperplasia.

According to specific embodiments, the gonadal toxicity is selected from the group consisting of hypogonadism, reduced spermatogenesis, reduced ovulation, premature ovarian failure and sterility.

According to a specific embodiment, the gonadal toxicity comprises reduced ovulation.

Methods of determining gonadal function are well known in the art and described e.g. in Bukman and Heineman, Human Reproduction Update, Vol. 7, No. 6, pp. 581-590; Target organ pathology, a basic text, Turton J and Hooson J (eds) Taylor & Francis, London, United Kingdom, 1998; and H. Marquardt, S. G. Schafer, R. O. McClellan, F. Welsch (eds.), "Toxicology", Chapter 13: The Liver, 1999, Academic Press, London. Gonadal function may be determined in a biological sample or an animal model or directly in the subject in need.

According to specific embodiments, the method further comprises determining gonadal function in the subject. Determining gonadal function may be effected prior, during and/or following treatment with the agent.

Thus, according to a specific embodiment, determining gonadal function is effected in-vivo (within the subject or animal model).

According to other specific embodiments, determining gonadal function is effected in-vitro or ex-vivo (on a biological sample derived from e.g. the subject).

According to a specific embodiment the biological sample comprises a blood sample (e.g. serum, plasma).

According to a specific embodiment, the biological sample comprises a follicular fluid.

According to another specific embodiment, the biological sample comprises a semen sample.

Non-limiting examples of techniques for determining gonadal function include hormonal evaluation; biochemical evaluation; imaging tests (e.g. ultrasound tests); ovarian biopsy; semen analysis; clinical investigations; and pathological and histopathological analysis.

According to specific embodiments, the gonadal function parameter is selected from the group consisting of hormonal evaluation, ultrasound evaluation and sperm analysis.

Method of hormonal evaluation are well known in the art and include measurement of levels of Follicle Stimulating Hormone (FSH), Luteinising Hormone (LH), FSH:LH ratios, progesterone, estrogen, oestradiol ($E_2$), B-hCG, anti Mullerian hormone (AMH), SHBG, 17-hydroxyprogesterone, free and total testosterone, DHEA-S, androstenedione, 3a,17(3-androstanediol glucuronide, cortisol, prolactin, and/or inhibin A and/or B, gonadotropin analogue stimulating test, the Clomiphene Challenge Test (CCT, a variation of baseline FSH measurement), the GnRH agonist stimulation test (GAST), the exogenous FSH Ovarian reserve test (EFORT). Hormonal evaluation is typically effected on blood samples.

According to specific embodiments, the hormonal evaluation is selected from the group consisting of LH, FSH, estradiol, AMH, testosterone, SHBG and progesterone.

As used herein the term "ultrasound evaluation" refers to ultrasound imaging of the reproductive organs and include, but not limited to, antral follicle count, measurement of the antral follicles or small follicles, ovarian volume, ovarian stromal peak systolic velocity including waveform and pulsatility index, ovarian follicular vascularity, morphology and thickness of the uterus and endometrium.

According to a specific embodiment, the ultrasound evaluation is antral follicle count.

As used herein the terms "sperm analysis" and "semen analysis" which may be used interchangeably, refer to determining concentration, morphology and/or motility of sperms in a semen sample.

According to specific embodiments at least one of the gonadal function parameters is used to determine gonadal function. According to other embodiments at least 2, at least 3, at least 4 or at least 5 of the parameters described above are used to determine gonadal function. According to specific embodiment, the gonadal function parameters used comprise hormonal evaluation and ultrasound evaluation or hormonal evaluation and sperm analysis.

As used herein the term "agent" refers to a substance that is used for the treatment of a disease (e.g., cancer) and has adverse toxic effect on the gonads. Non-limiting examples for such an agent include chemotherapy, radiotherapy, phototherapy and photodynamic therapy, surgery, nutritional therapy, ablative therapy, combined radiotherapy and chemotherapy, brachytherapy, proton beam therapy, immunotherapy, cellular therapy and photon beam radiosurgical therapy.

According to specific embodiments, the agent induces oxidative stress.

As used herein, the term "oxidative stress" refers to an imbalance between pro-oxidants such as reactive oxygen species (ROS) and defensive anti-oxidants in the gonads resulting in accumulation of ROS, DNA damage, lipid peroxidation, oxidation of proteins, activation of pro-apoptotic proteins and/or cell death. Methods of evaluating oxidative stress are well known in the art and described e.g. in Rakesh K. et al. A. Agarwal et al. (eds.), Studies on Women's Health, Oxidative Stress in Applied Basic Research and Clinical Practice, Chapter 2; and Sahoo D K, Protocols for Evaluating Antioxidant Defence and Oxidative Stress Parameters in Rat Testis, WebmedCentral BIOCHEMISTRY 2013; 4(5):WMC004265. Basically, these methods can be divided into screening assays, end product assays, activity of specific enzymes and metabolomics that utilize various markers of oxidative stress and include chemiluminescence, flow cytometry, ELISA, enzyme immunoassays (EIA), colorimetric assay, nuclear magnetic resonance (NMR) spectroscopy, HPLC, liquid chromatography-mass spectrometry (LC-MS) capillary electrophoresis-mass spectrometry (CE-MS) and gas chromatography-mass spectrometry (GC-MS); some of these can be tested using commercially available kits such as from Sigma-Aldrich, Promega, Abcam, Cayman Chemicals, Cell Biolabs, Applied Bioanalytical Labs.

Non-limiting examples of specific oxidative stress assays include chemiluminescence assay using a probe such as luminol (5-amino-2,3 dihydro-1,4 phthalazinedione) which reacts with free radicals thereby measuring global ROS; histochemical staining using Nitroblue tetrazolium (NBT) which is an electron acceptor that becomes reduced in the presence of ROS to form a blue-black compound, formazan, thereby detecting cells generating ROS; Immunohistochemistry or western blot analysis using specific antibodies to e.g. oxidative DNA adducts 8-hydroxy 2-deoxyguanosine; epifluorescence microscope detecting the presence of ROS by using a fluorescent end product of an oxidation reaction e.g. generated by the reaction of hydroethidine and a O2-, which yields ethidium bromide that emits a red fluorescent light; flow cytometry analysis detecting individual intracellular ROS radicals, e.g oxidation of 2, 7 dichlorofluorescein diacetate (DCFH-DA) by ROS makes the cells highly fluorescent and hereby can be used to measure formation of intracellular levels of hydrogen peroxide, Hydroethidine (HE) can be used for measurement of intracellular levels of superoxide as it is oxidized by the O2- to become ethidium bromide with red florescence emission; detecting activity of specific enzymes such as superoxide dismutase (SOD), glutathione peroxidase (GPx), catalase (CAT), thioredoxin reductases (TrxR), xanthine oxidase, NOS, superoxide dismutase, glutathione S-transferase, glucose-6-phosphate dehydrogenase (G6PD) activity; evaluating total antioxidant based on the ability of antioxidants in the sample to inhibit the oxidation of 2,20-azino-di-3-ethylbenzthiazoline sulphonate (ABTS) to ABTS+ by metmyoglobin; Griess reaction or chemiluminescence assay for determining metabolites of NO such as nitrite and nitrat; measuring lipid peroxides using e.g. Thiobarbituric acid-reacting substances (TBARS); measuring protein oxidation using e.g. protein carbonyl content as a marker; measuring lipid hydroperoxides; measuring total (free and esterified) 8-F2-Isoprostane, isoprostane $iPF_{2\alpha}$-VI, 8-hydroxy-2-deoxy guanosine (8-OH-dG), Fat-soluble antioxidants (vitamin A, vitamin E, beta-carotene, and lycopene); quantitation of pyruvate, $H_2O_2$ or free radicals scavengers, such as ascorbic acids, glutathione uric acid, vitamin-E and CoQ-10, content; and evaluation of cell viability and death using e.g. MTT test which is based on the selective ability of living cells to reduce the yellow salt MTT (3-(4, 5-dimethylthiazolyl-2)-2, 5-diphenyltetrazolium bromide) (e.g. Sigma, Aldrich St Louis, Mo., USA) to a purple-blue insoluble formazan precipitate, the TUNEL assay (e.g. Roche, Mannheim, Germany) and the Annexin V assay [e.g. ApoAlert® Annexin V Apoptosis Kit (Clontech Laboratories, Inc., Calif., USA)].

According to specific embodiments, the agent is selected from the group consisting of chemotherapy and radiotherapy.

As used herein the term "chemotherapy" refers to a cytotoxic or anti-neoplastic drug that is used in the treatment of a disease such as cancer.

Non-limiting examples for chemotherapy agents include: Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; B izele sin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etopo side Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofo sine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Peg asp argase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromyc in; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleuro sine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Non-limiting examples for chemotherapy approved drugs include: abarelix, aldesleukin, aldesleukin, alemtuzumab, alitretinoin, allopurinol, altretamine, amifostine, anastrozole, arsenic trioxide, asparaginase, azacitidine, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, go serelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trastuzumab, tretinoin ATRA, Uracil Mustard, valrubicin, vinblastine, vinorelbine, zoledronate and zoledronic acid.

According to specific embodiments, the chemotherapy is selected from the group consisting of mechlorethamine procarbazine cyclophosphamide, ifosfamide, busulfan, melphalan, chlorambucil, and chlormethine, doxorubicin, cisplatin and carboplatin.

According to specific embodiments, the chemotherapy is selected from the group consisting of Alkylating agents, Procarbazine, Platinum analogs and anthracycline antibiotics.

According to specific embodiments, the chemotherapy is selected from the group consisting of anthracycline antibiotics, alkylating agents, platinum-coordination complexes, epipodophyllotoxins and camptothecins.

According to a specific embodiment, the chemotherapy is doxorubicin.

As used herein the term "radiotherapy" refers to an exposure to high-energy radiation such as in the treatment of a disease (e.g., cancer). Non limiting examples for radiation include X-rays, Gamma-rays and charged particles. Exposure to radiation might be by an external-beam, by internal radiation therapy or by systemic radiation therapy using radioactive substances. According to specific embodiments of the present invention, radiation comprises total body irradiation (TBI) or local radiation wherein the gonads are close to or within the radiation field such as pelvic radiation.

Thus, according to a specific embodiment, the radiotherapy comprises total body irradiation (TBI).

According to another specific embodiment, the radiotherapy comprises pelvic irradiation.

As used herein, according to this aspect of the present invention, the phrase "subject in need thereof" refers to a mammalian male or female subject (e.g., human being) who has been treated or is expected to be treated with the gonadal toxicity inducing agent. The subject is typically at the reproductive age, however since PEDF prevents the detrimental effect induced to the gonads by the agent it can also be used in the treatment or prevention in male or female subject under the reproductive age. Veterinary uses are also contemplated.

According to specific embodiments the subject is a female.

According to other specific embodiments the subject is a male.

According to specific embodiments the subject is at a reproductive age.

As used herein the term "reproductive age" refers to the age at which the subject is capable of sexual reproduction to enable fertilization either naturally or by intervention.

According to specific embodiments, the female has not been subjected to oocyte retrieval.

According to other specific embodiments, the male has not been subjected to semen collection.

According to specific embodiments the subject is diagnosed with cancer.

The cancer can be any primary solid or non-solid cancer and/or cancer metastasis. Non-limiting examples of cancers include tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

According to specific embodiments, the cancer is selected from the group consisting of testicular cancer, breast cancer, ovarian cancer, lymphoma and leukemia.

According to specific embodiments the cancer is not osteosarcoma.

According to other specific embodiments the cancer is not prostate cancer.

According to other specific embodiments the cancer is not colon adenocarcinoma.

As mentioned the present inventors have also uncovered that PEDF can be used to protect and even alleviate uterus damage induced by treatment with tamoxifen.

Thus, according to another aspect of the present invention, there is provided a method of treating cancer in a subject in need thereof, the method comprising administering to the subject a therapeutically effective amount of tamoxifen and a therapeutically effective amount of pigment epithelium-derived factor (PEDF), thereby treating the cancer.

According to another aspect of the present invention, there is provided a tamoxifen and a pigment epithelium-derived factor (PEDF), for use in the treatment of cancer in a subject.

According to yet another aspect of the present invention, there is provided a method of treating or preventing tamoxifen-induced uterine toxicity in a subject in need thereof, the method comprising administering to the subject a therapeutically effective amount of pigment epithelium-derived factor (PEDF), thereby treating or preventing the tamoxifen-induced uterine toxicity in the subject.

According to another aspect of the present invention, there is provided a pigment epithelium-derived factor (PEDF) for use in the treatment or prevention of tamoxifen-induced uterine toxicity in a subject.

As used herein, the term "tamoxifen-induced uterine toxicity" refers to a temporary or permanent insult to the uterus that is induced by an exogenous administration of tamoxifen, a non-steroidal anti-estrogen agent. Typically, treatment of women with tamoxifen may lead to endometrial proliferation, endometrial hyperplasia, polyp formation and endometrial and uterine cancer, such as sarcoma and invasive carcinoma.

Uterine toxicity induced by tamoxifen may be evaluated by any method known in the art such as, but not limited to ultrasound (e.g. pelvic or transvaginal ultrasound) to see if the uterus contains a mass, or if the endometrium is thicker than usual; sonohysterography; endometrial biopsy; hysteroscopy; dilation and curettage (D&C); MRI; and high levels of blood CA125; as further described above.

According to specific embodiments, the method further comprises determining uterine toxicity in the subject. Determining uterine toxicity may be effected during and/or following treatment with tamoxifen.

Thus, according to a specific embodiment, determining uterine toxicity is effected in-vivo (within the subject or animal model).

According to other specific embodiments, determining uterine toxicity is effected in-vitro or ex-vivo (on a biological sample derived from e.g. the subject or animal model).

According to a specific embodiment, the biological sample comprises an endometrial biopsy.

As the present inventors have discovered that treatment with tamoxifen resulted in increased VEGF protein levels, decreased PEDF protein levels and increased VEGF/PEDF protein levels ratio.

Thus, according to another aspect of the present invention, there is provided a method of diagnosing tamoxifen-induced uterine toxicity in a subject, the method comprising determining the level of PEDF in a biological sample of the subject following treatment with tamoxifen, wherein a decrease below a predetermined threshold is indicative of the tamoxifen-induced uterine toxicity in the subject.

According to a specific embodiment, the method of diagnosing tamoxifen-induced uterine toxicity further comprises determining the level of VEGF in the biological sample, wherein an increase above a predetermined threshold is indicative of the tamoxifen-induced uterine toxicity in the subject.

According to another specific embodiment, an increase in the ratio between VEGF and PEDF above a predetermined threshold in the biological sample is indicative of the tamoxifen-induced uterine toxicity in the subject.

"Vascular endothelial growth factor (VEGF)", also known as VEGF-A, Vascular permeability factor, VPF, and MVCD1, refers to the polynucleotide and an expression product e.g. polypeptide of the VEGFA gene. According to a specific embodiment, the VEGF protein refers to the human protein, such as provided in the following GenBank Numbers NP_001020537 (SEQ ID NO: 29), NP_001020538 (SEQ ID NO: 30), NP_001020539 (SEQ ID NO: 31), NP_001020540 (SEQ ID NO: 32), NP_001020541 (SEQ ID NO: 33), NP_001028928 (SEQ ID NO: 34), NP_001165093 (SEQ ID NO: 35), NP_001165094 (SEQ ID NO: 36), NP_001165095 (SEQ ID NO: 37), NP_001165096 (SEQ ID NO:38), NP_001165097 (SEQ ID NO: 39), NP_001165098 (SEQ ID NO: 40), NP_001165099 (SEQ ID NO: 41), NP_001165100 (SEQ ID NO: 42), NP_001165101 (SEQ ID NO: 43), NP_001191313 (SEQ ID NO: 44), NP_001191314 (SEQ ID NO: 45), NP_001273973 (SEQ ID NO: 46) and NP_003367 (SEQ ID NO:47).

As used herein the term "diagnosing" refers to determining presence or absence of a pathology (e.g., a disease, disorder, condition or syndrome, e.g., uterine toxicity), classifying a pathology or a symptom, determining a severity of the pathology, monitoring pathology progression, forecasting an outcome of a pathology and/or prospects of recovery and screening of a subject for a specific disease.

As used herein, the phrases "level of PEDF" or "level of VEGF" refer to the degree of gene expression and/or gene product activity of PEDF or VEGF, respectively, in a biological sample. Accordingly, the level of PEDF and/or VEGF can be determined at the amino acid level using protein detection methods.

Thus, the level of PEDF and/or VEGF amino acid sequence (protein) can be determined using a PEDF or VEGF specific antibodies via the formation of an immunocomplex [i.e., a complex formed between the PEDF antigen present in the biological sample and the PEDF specific antibody or a complex formed between the VEGF antigen present in the biological sample and the VEGF specific antibody].

The immunocomplex of the present invention can be formed at a variety of temperatures, salt concentration and pH values which may vary depending on the method and the biological sample used and those of skills in the art are capable of adjusting the conditions suitable for the formation of each immunocomplex.

According to the method of this aspect of the present invention, detection of immunocomplex formation is indicative of a diagnosis of the tamoxifen-induced uterine toxicity. Various methods can be used to detect the formation of the PEDF and/or the VEGF immunocomplex of the present invention and those of skills in the art are capable of determining which method is suitable for each immunocomplex and/or the type of cells used for diagnosis.

The antibody used in the immunocomplex of the present invention can be labeled using methods known in the art. It will be appreciated that the labeled antibodies can be either primary antibodies (i.e., which bind to the specific antigen, e.g., a PEFD-specific antigen or a VEGF-specific antigen) or secondary antibodies (e.g., labeled goat anti rabbit antibodies, labeled mouse anti human antibody) which bind to the primary antibodies. The antibody can be directly conjugated to a label or can be conjugated to an enzyme.

Detection of the PEDF and/or VEGF immunocomplex in a biological sample can be performed using method well known in the art and include, but not limited to, fluorescence activated cell sorting (FACS), enzyme linked immunosorbent assay (ELISA), Western blot and radio-immunoassay (RIA) analyses, immunoprecipitation (IP), immunohistochemistry, or by a molecular weight-based approach.

Alternatively or additionally, the level of PEDF and/or VEGF can be determined at the nucleic acid level using mRNA detection methods.

RNA or cDNA detection methods can be performed using an isolated polynucleotide (e.g., a polynucleotide probe, an oligonucleotide probe/primer) capable of hybridizing to a PEDF or VEGF nucleic acid sequence such as the PEDF transcript set forth by SEQ ID NO: 1, the VEGF transcript set forth by SEQ ID NO: 28 (NM_001025366) or a portion thereof in the biological sample. Such a polynucleotide can be at any size, such as a short polynucleotide (e.g., of 15-200 bases), an intermediate polynucleotide of 100-2000 bases and a long polynucleotide of more than 2000 bases.

Determining the level of PEDF and/or VEGF in either the amino acid or the nucleic acid level is effected in a biological sample taken from a subject which is diagnosed with cancer and may be treated with uterine-inducing toxicity agents.

The isolated polynucleotide probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the PEDF or VEGF RNA transcript of the present invention.

Oligonucleotides designed according to the teachings of the present invention can be generated according to any oligonucleotide synthesis method known in the art such as enzymatic synthesis or solid phase synthesis.

The isolated polynucleotide used by the present invention can be labeled either directly or indirectly using a tag or label molecule.

The above-described polynucleotides can be employed in a variety of RNA and cDNA detection methods such as Northern blot analysis, reverse-transcribed PCR (RT-PCR) [e.g., a semi-quantitative RT-PCR, quantitative RT-PCR using e.g., the Light Cycler™ (Roche)], RNA in situ hybridization (RNA-ISH), in situ RT-PCR stain [e.g., as described in Nuovo G J, et al. 1993, Intracellular localization of polymerase chain reaction (PCR)-amplified hepatitis C cDNA. Am J Surg Pathol. 17: 683-90, and Komminoth P, et al. 1994, Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract., 190: 1017-25] and oligonucleotide microarray analysis [e.g., using the Affymetrix microarray (Affymetrix®, Santa Clara, Calif.)].

As used herein the phrase "a decrease below a predetermined threshold" refers to a decrease in expression of PEDF which is higher than a predetermined threshold such as at least 5%, at least 10%, at least 20%, at least 30%, at least 40%, at least 50%, at least 60%, at least 70%, at least 80%, at least 90%, at least 95%, or 100%, relative to the expression of PEDF in a control sample taken from a healthy subject not treated with tamoxifen or from the same subject before treatment with tamoxifen. Such control level can be obtained from the scientific literature.

As used herein the phrase "an increase above a predetermined threshold" refers to an increase in expression of VEGF which is higher than a predetermined threshold such as at least 5%, at least 10%, at least 20%, at least 30%, at least 40%, at least 50%, at least 60%, at least 70%, at least 80%, at least 90%, at least 95%, at least 100% or more, relative to the expression of VEGF in a control sample taken from a healthy subject not treated with tamoxifen or from the same subject before treatment with tamoxifen. Such control level can be obtained from the scientific literature.

It will be appreciated that the presence of the tamoxifen-induced uterine toxicity can be further validated using additional assays e.g. ultrasound, endometrial biopsy and hysteroscopy.

As used herein, according to this aspect of the present invention, the phrase "subject in need thereof" refers to a mammalian female subject (e.g., human being) who has been treated or is expected to be treated with tamoxifen. Veterinary uses are also contemplated.

The subject may be at the reproductive age, under the reproductive age or above the reproductive age.

According to specific embodiments the subject is at a reproductive age.

According to other specific embodiments, the subject is at the pre-menopausal period. In human, the pre-menopausal period is before the age of 45-55 for most women.

According to yet other specific embodiments, the subject is at the post-menopausal period. In human menopause is defined as the state of an absence of menstrual periods for 12 months and in most women the post-menopausal period start between the ages of 45 and 55.

According to specific embodiments the subject is diagnosed with cancer.

According to a specific embodiment, the cancer is breast cancer.

The term "treating" refers to inhibiting or arresting the development of a pathology (disease, disorder, or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease. According to specific embodiments, the method or use further comprising administering the agent (i.e., which induces gonadal toxicity) or the uterine inducing toxicity agent e.g., tamoxifen to the subject.

According to specific embodiments PEDF is administered concomitant with the agent or the tamoxifen.

According to other specific embodiments PEDF is administered following first, second or multiple administrations of the agent or the tamoxifen.

According to another specific embodiments, PEDDF is administered prior administration of the agent or the tamoxifen.

According to specific embodiments PEDF is administered after accumulation of oxidants in the gonads above a predetermined threshold.

As used herein the phrase "accumulation above a predetermined threshold" refers to a fold increase which is higher than a predetermined threshold such as at least about 1.2, at least about, at least about 1.8, at least about twice, at least about three times, at least about four time, at least about five times, at least about six times, at least about seven times, at least about eight times, at least about nine times, at least about 20 times, at least about 50 times, at least about 100 times, at least about 200 times, at least about 350, at least about 500 times, at least about 1000 times, at least about 2000 times, at least about 3000 times relative to a suitable control e.g. the level before treatment with the agent, the level at the beginning of a culture.

According to specific embodiments, PEDF can be used alone or in combination with other established or experimental therapeutic regimen to treat or prevent gonadal toxicity or ovarian toxicity, such as GnRH agonist protection.

PEDF and the agent or the tamoxifen can be administered to the subject per se, or in a pharmaceutical composition where each or both are mixed with suitable carriers or excipients.

As used herein a "pharmaceutical composition" refers to a preparation of the active ingredient described herein with other chemical components such as physiologically suitable carriers and excipients. The purpose of a pharmaceutical composition is to facilitate administration of a compound to an organism.

Herein the term "active ingredient" refers to the PEDF, the agent and/or the tamoxifen accountable for the biological effect. The active ingredients may be co-formulated or in separate formulation.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a specific embodiment, administering the PEDF is effected by subcutaneous injection.

According to another specific embodiment, administering the PEDF is effected by intravenous injection.

Alternately, one may administer the pharmaceutical composition in a local rather than systemic manner, for example, via injection of the pharmaceutical composition directly into a tissue region of a patient (e.g., gonads).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose.

As used herein, the phrase "therapeutically effective amount" refers to an amount of active ingredients (e.g., PEDF) effective to prevent, alleviate or ameliorate symptoms of a disorder (i.e., gonadal toxicity, ovarian toxicity or cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals (as described in the Examples section which follows). The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, and the type of agent used dosing can be of a single or a plurality of administrations, with course of treatment lasting from several days to several weeks or until cure is effected or diminution of the disease state is achieved using range of dosages such as a minimum effective dose (MED), median effective dose, a sub-maximal dose, maximum tolerated dose (MTD) or optimum biologic dose (OBD).

According to a specific embodiment, the agent or the tamoxifen is administered in a MTD. As used herein the term "maximum tolerated dose" or "MTD" refers to the highest dose of an agent that is effective but does not cause excessive toxicity intolerable to the subject. Generally, an MTD can be determined by standard pharmaceutical procedures in vitro, in cell cultures or experimental animals. Generally, MTD is subject specific and is adjusted for the patient's body surface area; a measurement that correlates with blood volume. Ultimately, the MTD can be determined by those having the requisite skill and experience, such as a physician (e.g. oncologist).

Exemplary doses of PEDF are provided infra:
0.02-0.4 mg/kg/day, 0.162-0.32 mg/kg/day, 0.01-0.2 mg/kg/day, 0.1-0.4 mg/kg/day, 0.2-0.4 mg/kg/day or 0.05-0.1 mg/kg/day.

According to a specific embodiment, the PEDF is administered at a dosage range of 0.02-0.4 mg/kg/day.

According to another specific embodiment, the PEDF is administered at a dosage range of 0.162-0.32 mg/kg/day.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to an aspect of the present invention there is provided an article of manufacture packaging tamoxifen and PEDF for use in treating cancer.

Also provided is an article of manufacture packaging the agent and PEDF identified for use in the treatment or prevention of gonadal toxicity induced by the agent. The agent or the tamoxifen and the PEDF can be packaged in separate containers of in c-formulation. The article may be accompanied by instructions for use.

According to another aspect of the invention there is provided a method of improving oocyte quality, the method comprising ex-vivo contacting an oocyte in a cell culture comprising said oocyte with an effective amount of pigment epithelium-derived factor (PEDF), thereby improving oocyte quality ex-vivo.

As used herein, the term "an oocyte" refers to an unfertilized oocyte, a fertilized oocyte (also referred to as one cell zygote) and an embryo at any stage of development, including the stages of cleavage until the blastocyst stage.

As used herein, the singular form "an oocyte" includes a single oocyte and a plurality of oocytes for examples at least 2, at least 3, at least 4, at least 5, at least 10, at least 15, at least 20 oocytes or more.

According to specific embodiments the oocyte is comprised in an ovary or an ovary fragment.

According to specific embodiments the oocyte is isolated.

According to a specific embodiment, contacting an oocyte with PEDF is effected in-vitro or ex-vivo. Thus, the PEDF is added such that PEDF is in direct contact with the oocyte. According to a specific embodiment, the PEDF is added at an anti-oxidative amount.

As used herein, the term "anti-oxidative amount" refers to an amount leading to a decrease of at least 5% in oxidative stress in comparison to a suitable control e.g. in the absence of PEDF. The decrease in oxidative stress may be in the cell culture in general and/or in the oocyte in particular. According to a specific embodiment, the decrease is in at least 10%, 30%, 40% or even higher say, 50%, 60%, 70%, 80%, 90% or more than 100%. Decreased oxidative stress may be manifested in the form of e.g. an increase in anti-oxidants and/or a decrease in ROS, DNA damage, lipid peroxidation, oxidation of proteins, activation of pro-apoptotic proteins and/or cell death; as further detailed hereinabove.

According to another aspect of the present invention there is provided a cell culture comprising an oocyte and an exogenously added PEDF.

As used herein, the term "cell culture" refers to a cell population comprising an oocyte that is grown under controlled conditions outside of its natural environment (i.e. in-vitro or ex-vivo). Typically, the cell population is grown with appropriate defined culture medium containing nutrients that nourish the oocyte which support its survival and optimally fertilization. According to specific embodiments, the cell culture is a mammalian cell culture (e.g. human).

According to specific embodiments the oocyte is maintained under conditions for in-vitro fertilization (IVF).

IVF techniques are known to anyone skilled in the arts. Typically, the female is first treated with fertility drugs to stimulate maturation of multiple oocytes. Drug type and dosage vary depending on the patient profile and the stimulation protocol used. These oocytes are then surgically recovered by microsurgical techniques (e.g. transvaginal oocyte retrieval) directly from the ovary. The recovered oocytes are then placed into a suitable culture dish and exposed to sperm collected from the male for fertilization. The day of oocyte collection and insemination is day 0. In many cases an additional procedure known as intracytoplasmic sperm injection (ICSI) is required to increase the chances of fertilization. After fertilization occurs, the fertilized oocyte is allowed to grow to a multicelled embryo for approximately 3-5 days. During this time culture conditions and embryos are evaluated continuously. Following, the embryos are recovered and returned to the female, where implantation of the embryo on the wall of the uterus is expected to occur, resulting, from that time forward, in a normal pregnancy. For additional details on methods involved in IVF procedures see Kuldeep Jain and Pankaj Talwar (IVF techniques for the beginner, JP Medical Ltd 2013).

As used herein, the phrase "maintained under conditions for IVF" refers to conditions which allow fertilization of an oocyte by a sperm, division of a fertilized oocyte and/or development of an embryo until a certain stage of maturity outside the body.

According to specific embodiments, the oocyte is maintained under conditions which allow development of a zygote, a cleavaging stage embryo, or a blastocyst.

According to specific embodiments, the contacting is effected before fertilization of the oocyte.

According to specific embodiments the contacting is effected following fertilization of the oocyte.

According to other specific embodiments, the contacting is effected concomitant with fertilization of the oocyte.

According to specific embodiments, the contacting is effected following accumulation of oxidants in the culture above a predetermined threshold.

According to specific embodiments, the contacting is effected prior to freezing or during thawing or following thawing of the oocyte.

According to another aspect of the present invention there is provided an IVF grade medium for use in IVF comprising PEDF.

Also provided is a kit comprising:
(i) An IVF grade medium for use in IVF; and
(ii) PEDF.

As used herein the term "IVF grade medium" refers to a medium suitable for in vitro incubation and culture of gametes or embryos during IVF procedures (e.g., in human beings). A range of suitable media are available, the types and compositions of which are well known to those of skill in the art. According to a specific embodiment, the culture medium contains at least water, salts, nutrients, essential amino acids, vitamins and hormones, and may also include one or more growth factors. A suitable medium might include, but is not limited to, HTF medium; Modified Whittens medium; Whittinghams T6 medium; Hams F10; Earles solution; Hams-Flo; IVF50; G1.1; G1.2; G2.2; Cook's IVF media (e.g. Sydney IVF Cleavage, Sydney IVF Blastocyst, Sydney IVF Fertilization); FertiPro IVF media (e.g. FertiCult™ IVF, FertiCult™ G3); Gynemed IVF media (GM501 Basic, GM501 Cult); InVitroCare IVF media (e.g. IVC-ONE™, IVC-TWO™, IVC-THREE™); Irvine IVF media (e.g. P1 ®, ECM®, SSM™, MultiBlastw®, HTF); Life Global IVF media (Global®, Global® for Fertilization, Global® HP, Global® Total® for Fertilization, Global® for Fertilization, Global® Collect®, Global® Total® w/HEPES, Global® w/HEPES, Blastocyst, HTF, HTFxtra); Origio IVF media (Universal IVF, ISM1™, ISM1™, EmbryoAssist™, BlastAssist®, EmbryoGen®); Sage IVF media (e.g. Quinns Advantage® Fert, Quinns Advantage® Cleavage, Quinns Advantage® Blastocyst); and Vitrolife IVF media (e.g. G-GAMETE™, G-MOPS™, G-IVF™ PLUS, G-1™, G-2™ PLUS, IVF™, and CCM™).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Reagents—
H$_2$O$_2$, Dulbecco's modified Eagle's medium/Ham F12 1:1 (DMEM-F12), Dulbecco's phosphate-buffered saline (DPBS), penicillin and streptomycin (Biological Industries, Beit-Ha'emek, Israel). Charcoal-stripped fetal bovine serum (CS-FBS; Invitrogen, Grand Island, N.Y., USA). Doxorubicin (DXR, Teva Israel).

Primary Antibodies—
anti PNPLA2, anti actin (ABD66 and MAB1501, respectively; Millipore, Temecula, Calif., USA), anti Pho-AKT and anti Gen-AKT (P4112 and P1601, respectively; Sigma, St Louis, Mo., USA) and anti BAX (sc-526, Santa Cruz Biotechnology, Santa Cruz, Calif., USA), anti PEDF (sc-25594, Santa Cruz Biotechnology), anti-VEGF (sc-152, Santa Cruz Biotechnology), anti-CD34 (CL8927AP; Cedarlane Laboratories, N.C., USA) and anti-ERα (ab 1746, Abcam, Cambridge, UK).

Secondary Antibodies—
HRP-conjugated monoclonal and polyclonal antibodies (Jackson Immunoresearch, Pa., USA). Goat anti rabbit Alexa Flour 488-conjugated antibodies, goat anti-rat Alexa Flour555-conjugated (Cell signaling technology, MA, USA). Hoechst 3342 (Sigma).

Animals—
DXR damage was evaluated in 7 weeks ICR female mice following treatment for superovulation with pregnant mares' serum (PMSG, 7 IU) SC on day 0 and human chorionic gonadotropin (hCG, 7IU) SC on day 2. On day 1, mice were administered with DXR (6 mg/kg) or saline (control) IV. Mice ovaries were retrieved on day 3 (FIG. 1A). The ability of rPEDF to overcome the destructive effect of DXR 7 weeks ICR female mice were treated with DXR (6 mg/kg) or saline (control) IV on day 0, rPEDF (2 mg/kg) or TRIS (control) was administered SC on day 1, followed by induction for superovulation with PMSG (7 IU) SC on day 4 and hCG (7 IU) SC on day 6. Mice ovaries were retrieved on day 7 (FIG. 2A). The sub-acute effect of tamoxifen on post-menopausal uterine tissue was evaluated in ovariectomized (OVX) ICR mice treated daily for 7 days with various concentrations of tamoxifen (0.3-3.3 μg/kg). Mice uteri were excised at day 7. To evaluate the effect of rPEDF administration in the sub-acute model, OVX mice were treated daily for 7 days with tamoxifen (2.5 μg/mouse) and rPEDF (10 mg/kg) SC. Mice treated with tamoxifen alone served as control. The prolonged effect of tamoxifen on post-menopausal uterine tissue was evaluated in OVX ICR mice treated with tamoxifen (2.5 μg/mouse) 5 days per week for one month. To evaluate the effect of rPEDF administration in the prolonged model, mice were further treated with rPEDF (2 mg/kg) SC once every 3 days for one month starting on day 8 of tamoxifen treatment. Mice treated with tamoxifen alone served as control.

Evaluation of the Number of Ovulated Oocytes—
cumulus-enclosed oocytes were isolated from the oviductal ampullae into M2 medium (Sigma), 16-18 hrs after hCG administration. Cumulus cells were removed by a brief exposure to 400 IU/ml hyaluronidase (Sigma) and the number of ovulated oocytes was counted under binocular.

Cell Culture—
Rat granulosa cell line LH-15 [Suh et al. J Cell Biol (1992) 119: 439-450] was cultured in hormone-free DMEM-F12 medium, supplemented with penicillin (100 IU/ml; Biological Industries), streptomycin (100 mg/ml; Biological Industries) and 10% charcoal-stripped fetal bovine serum (CS-FBS; Invitrogen) (culture medium), as described previously (Breckwoldt et al. 1996, Sasson & Amsterdam 2002). Cells were serum-starved for 16 hours (0.1% CS-FBS) prior to and during recombinant PEDF (rPEDF) stimulation or incubated in 2% CS-FBS during H$_2$O$_2$ stimulation.

Western Blot Analysis—
Samples were homogenized in cold lysis buffer (20 mM HEPES, 150 mM NaCl and 0.2% Igepal; sigma) and centrifuged at 12,000 rpm, for 15 min, at 4° C.). Proteins were separated by sodium dodecyl sulfate polyacrylamide gel electrophoresis (SDS-PAGE; 10%; Bio-Rad, Israel). Separated proteins were transferred onto nitrocellulose membranes (Whatman GmbH, Germany) in a mini tank transfer unit (TE 22, Amersham, UK). Approximate molecular masses were determined by comparison with the migration of pre-stained protein standards (Bio-Rad). Blots were blocked for 1 hour in TBST (10 mM Tris-HCl, pH=8.0, 150 mM NaCl, 0.05% Tween 20) containing 5% skim-milk (Alba, N.Y., USA) followed by an over-night incubation at 4° C. with primary antibodies. Blots were washed three times in TBST and incubated for 1 hour at room temperature with horseradish peroxidase-conjugated secondary antibodies. Immunoreactive bands were visualized by enhanced chemiluminescence (ECL; Thermo Scientific, Ill., USA) according to manufacturer's guidelines. Intensity of the protein bands was quantified by Image J sportswear (NIH).

Immunohistochemistry—
Paraffin-embedded sections were deparaffinized, microwave heated while being subjected to an antigen retrieval agent (H-3300, Vector Laboratories Inc., Burlingame, Calif., USA), cooled on ice to room temperature, rinsed in PBS, incubated for 1 hour with PBSTg (0.2% Tween and gelatin in PBS), washed with PBS, blocked for 10 minutes in blocking solution (Cell Marque Corporation, Calif., USA)

and incubated overnight with anti PNPLA2 or anti-CD34 primary antibodies. On the following day, sections were washed in PBSTg and PBS before and after applying the appropriate secondary antibodies (goat anti-rat Alexa Flour555-conjugated, Goat anti rabbit Alexa Flour 488-conjugated antibodies (Cell signaling technology) together with a nuclear marker (Hoechst 3342, sigma), rinsed, mounted with Mowiol (Sigma), visualized and photographed by a Leica laser confocal microscope (SP5 Wetzalr, Germany) that was calibrated to a secondary antibody-only control.

PEDF Production—

Human recombinant PEDF (NM_002615.4, SEQ ID NO: 1) was expressed in *E. coli* BL21. Bacteria were allowed to grow at 300 C to OD600 nm of 0.5-0.6, induced for 4-5 hours by 0.5 mmol/L isopropyl-L-thio-β-D-galactopyranoside, centrifuged and their pellets were lysed. Recombinant proteins were purified by ion metal affinity chromatography with Ni-NTA His-Bind resin (Merck KgaA, Darmstadt, Germany) according to the manufacturer's protocol. Eluted fractions were resolved by SDS-PAGE followed by GelCode (Blue Stain Reagent, Thermo scientific) or western blotted with a specific anti PEDF antibody. Eluates with >90% purity were dialyzed against TRIS buffer pH=10 [Konson et al. Cancer Res (2010) 70 6247-6257].

RNA Isolation, Reverse Transcription (RT), PCR and Real-Time Polymerase Chain Reaction (qPCR)—

Total RNA was isolated from various tissues (ovaries, eyes) or from granulosa cells, using Trizol reagent (Invitrogen) according to manufacturer's instructions, and quantified with the Nano-Drop spectrophotometer (ND-1000; Thermo Scientific). First-strand cDNA was produced by RT (Maxima™ Reverse transcriptase, Thermo Scientific) from a total of 1 μg RNA, using oligo-dt primers (Thermo Scientific). DNA was amplified using 1 μl RT reaction and 50 pmol gene-specific primers in ReadyMix™ mixture (Sigma). Polymerase Chain Reaction (PCR) products were separated by 1.5% agarose gel electrophoresis and visualized by ethidium bromide staining. Changes in the level of expression of mRNA were detected by SYBR green reagent (SYBR® Green PCR Master Mix, ABI, Carlsbad, Calif., USA) along with 15 ng cDNA and specific primers, on a StepOnePlus Real-Time PCR System (Applied Biosystems, Foster City, Calif., USA).

TABLE 1

PCR primers

| | | | |
|---|---|---|---|
| SEQ ID NO.: 2 | Forward: 5' GTGAAGGTCGGTGTGAACGG 3' | mouse/ rat | GPDH (536 bp) |
| SEQ ID NO.: 3 | Reverse: 5' GTGATGGCATGGACTGTGGTC 3' | | |
| SEQ ID NO.: 4 | Forward: 5' TGTGGCCTCATTCCTCCT 3' | mouse | PEDF-R (111 bP) |
| SEQ ID NO.: 5 | Reverse: 5' TGAGAATGGGGACACTGT 3' | | |

TABLE 2

RT-PCR primers

| | | | |
|---|---|---|---|
| SEQ ID NO.: 6 | Forward: 5' CTCATGGACTGATTATGGACAGGA 3' | mouse/ rat | HPRT1 |
| SEQ ID NO.: 7 | Reverse: 5' GCAGGTCAGCAAAGAACTTATAGCC 3' | | |
| SEQ ID NO.: 8 | Forward: 5' TTCACCCGGAGCAGTGAT 3' | rat | PEDF |
| SEQ ID NO.: 9 | Reverse: 5' GCCTCCAGAATTGTGTTTGAG 3' | | |
| SEQ ID NO.: 10 | Forward: 5' CCAAGTCTCTGCAGGACATGAAG 3' | mouse | PEDF |
| SEQ ID NO.: 11 | Reverse: 5' GGTTTGCCAGTAATCTTGCTG 3' | | |
| SEQ ID NO.: 12 | Forward: 5' AACCAGTTGTGGTGTCAGGAC 3' | rat | SOD-1 |
| SEQ ID NO.: 13 | Reverse: 5' CCGCCATGTTTCTTAGAGTGAGG 3' | | |
| SEQ ID NO.: 14 | Forward: 5' CCACCGTGTATGCCTTCTCC 3' | rat | GPX-1 |
| SEQ ID NO.: 15 | Reverse: 5' AGAGGGACGCGACATTCTCAAT 3' | | |
| SEQ ID NO.: 16 | Forward: 5' TGTTTCAGACGGAGAGAACGTC 3' | mouse | PNPLA2 |
| SEQ ID NO.: 17 | Reverse: 5' TGAGAATGGGGACACTGTGATG 3' | | |
| SEQ ID NO.: 18 | Forward: 5' CCTGGGACCTTCACTAACCA 3' | mouse | Laminin receptor |
| SEQ ID NO.: 19 | Reverse: 5' CAGCATCCACCACATCAGAC 3' | | |
| SEQ ID NO.: 20 | Forward: 5' CTTCAGTGCCAACAGCCT 3' | mouse | ERα, |
| SEQ ID NO.: 21 | Reverse: 5' GACAGTCTCTCTCGGCCAT 3' | | |
| SEQ ID NO.: 22 | Forward: 5' GCCAACCTCCTGATGCTTCTTT 3' | mouse | ERβ |
| SEQ ID NO.: 23 | Reverse: 5' TTGTACCCTCGAAGCGTGTGA 3' | | |
| SEQ ID NO.: 24 | Forward: 5' GGTGGGCCTTCCTAACGAG 3' | mouse | PR |
| SEQ ID NO.: 25 | Reverse: 5' GACCACATCAGGCTCAATGCT 3' | | |

MTT Cell Proliferation Assay—

Equal amount of LH-15 cells were seeded onto 6-well plates to a final volume of 500 μl. Following treatments, each well was incubated for 30 minutes with 10 μl of MTT [3-(4, 5-Dimethylthiazol-2-yl)-2, 5-diphenyltetrazolium bromide; 5 mg/ml] followed by an additional 2-4 hours incubation period at 37° C. The reaction was terminated by addition of 110 μl HCl (0.07 M in isopropanol) and OD 560 nm was measured by the SpectraMax 190 microplate reader (Molecular Probes, Eugene, Oreg., USA).

Evaluation of Uterine Weight—

At the end of each experiment, uteri were isolated, excised and weighed.

Statistical Analysis—

Differences in the intensity of the protein bands were assessed using the t test, with a significance of $P<0.05$. Each experiment was repeated at least three times, and the intensity was expressed as percentage of intensity of the control, which was arbitrarily set as 100%.

Example 1

The Effects of Dxr and Exogenous Pedf on Mice Ovaries

DXR Reduces PEDF mRNA Level in Mice Ovaries

To evaluate the damage inflicted by DXR on mice ovaries PEDF mRNA level was evaluated in mice ovaries retrieved from mice treated for superovulation with standard PMSG/hCG protocol [Ben-Aharon et al. Reproductive biology and endocrinology: RB&E (2010) 8: 20], followed by treatment with DXR (FIG. 1A). As demonstrated in FIG. 1B, DXR significantly ($P<0.05$) reduced PEDF mRNA level.

Exogenous PEDF Improves Ovulation Under DXR Conditions

Based on the negative effect of DXR on the level of PEDF mRNA, the ability of exogenous recombinant PEDF (rPEDF) to overcome the destructive effect of DXR on ovulation was explored. To this end, female mice were treated with DXR followed by administration of rPEDF the day after. On the fourth day of the experiment mice were induced for superovulation with the standard PMSG/hCG protocol [Ben-Aharon et al. Reproductive biology and endocrinology: RB&E (2010) 8: 20]. Mice were sacrificed 16-17 hours after hCG administration (FIG. 2A). As demonstrated in FIG. 2B, rPEDF significantly ($P<0.05$) decreased DXR-induced reduction in number of ovulated oocytes.

Example 2

The Effects of Oxidative Stress and Exogenous PEDF on LH-15 Rat Granulosa Cells $H_2O_2$ Affects the Viability of LH-15 Cells and the mRNA Levels of PEDF in these Cells To evaluate the damage inflicted by oxidative stress (OS) on granulosa cells a MTT assay was employed and cells viability was followed. Exposure of rat granulosa cell line (referred to as "LH-15 cells") to increasing doses of $H_2O_2$ (100-500 µM) for 24 hours caused a statistically significant ($P<0.05$), dose dependent, decrease in cells viability (FIG. 3A). Furthermore, $H_2O_2$ significantly ($P<0.01$) reduced PEDF mRNA level, already at a concentration of 100 µM (FIG. 3B).

Exogenous PEDF Attenuates $H_2O_2$-Induced Cytotoxicity in LH-15 Cell

Based on the negative effect of $H_2O_2$ on the viability of LH-15 cells and the level of PEDF mRNA, the ability of exogenous recombinant PEDF (rPEDF) to overcome the destructive effect of $H_2O_2$ in granulosa cells was explored. To this end, LH-15 cells were incubated with 100 or 200 µM $H_2O_2$ for 24 hours in the presence or absence of rPEDF (1 nM or 5 nM) and cells viability was evaluated by the MTT assay. As demonstrated in FIG. 4A, rPEDF significantly ($P<0.05$) decreased $H_2O_2$-induced reduction in cells viability. In addition, the expression of the pro-apoptotic protein, BAX and the mRNA levels of the anti-oxidants enzymes SOD-1 and GPX-1 in LH-15 cells under the same stimulatory conditions were followed. The results indicated that while BAX level was elevated following $H_2O_2$ treatment, exogenous addition of rPEDF decreased its expression (FIGS. 4B-C; $P<0.05$). In contrast, SOD-1 and GPX-1 mRNA levels were decreased following $H_2O_2$ treatment; exogenous addition of rPEDF elevated their expression (FIGS. 5A-B).

Example 3

PEDF Receptor, PNPLA2, is Expressed in Mouse Ovaries and Rat Granulosa Cells The PEDF Receptor, PNPLA2, is Expressed in Mouse Ovaries The pro-survival PEDF-R, Patatin-like phospholipase domain-containing protein 2 (PNPLA2), expression in mice ovaries was evaluated at the protein and mRNA levels. Immunostaining of mice ovaries revealed that the pro-survival PEDF-R, PNPLA2 is expressed in granulosa cells, theca cells and oocytes (FIG. 6A). Furthermore, mouse ovaries express PEDF-R mRNA (FIG. 6B) and protein (FIG. 6C).

PEDF Receptor, PNPLA2, is Expressed in LH-15 Cells

The observed effect of rPEDF on LH-15 cells suggests that granulosa cells express PEDF receptor/s (PEDF-R). As demonstrated in FIGS. 6B-C, granulosa cells express the pro-survival PEDF-R, PNPLA2, mRNA (FIG. 6B) and protein (FIG. 6C).

Exogenous PEDF Activated AKT in Granulosa Cells

Having shown that granulosa cells express PNPLA2 that mediates PEDF pro-survival functions, the ability of rPEDF to activate AKT, a known factor in the pro-survival signaling pathway (Li et al. Stem Cells 2013), was examined. To this end, serum-starved LH-15 cells were stimulated with 1 nM rPEDF for various durations. The results indicated that stimulation with rPEDF induced prolonged, time-dependent phosphorylation of AKT starting at 5 minutes (FIGS. 7A-B; $P<0.05$).

Thus, without being bound by theory, heading towards possible mechanism, rodents granulosa cells, theca cells and oocytes express the pro-survival PEDF receptor, PNPLA2; and once stimulated by rPEDF, granulosa cells exhibit phosphorylation of AKT, a central pro-survival mediator of cell signaling.

Example 4

The Effects of Tamoxifen and Exogenous Pedf on Mice Uterine Tissue

Sub-Acute Tamoxifen Treatment Affects Uterine Weight and VEGF and PEDF Expression To evaluate the effect of sub-acute administration of tamoxifen on post-menopausal uterine tissue, ovariectomized (OVX) mice were treated daily for 7 days with various concentrations of tamoxifen. As demonstrated in FIG. 8, a dose dependent increase of uterine weight was observed following sub-acute tamoxifen administration. In addition, the level of uterine VEGF protein was up-regulated in a dose dependent manner (FIG. 9A-B), positively correlating with uterine weight. On the other hand, the expression of PEDF protein was down-regulated (FIGS. 9A and 9C) as tamoxifen doses were increased. This reciprocal change in the VEGF and PEDF protein levels in uteri following sub-acute tamoxifen administration resulted in a dramatic significant dose dependent increase in the ration of VEGF/PEDF protein levels (FIG. 9D).

As PEDF a secreted glycoprotein with autocrine and paracrine activities, the effect of tamoxifen on expression levels of receptors essential for PEDF activity was evaluated. PEDF was shown to function either as a pro-survival factor through the PNAPLA2 receptor, or as an anti-angiogenic factor through Laminin receptor. As shown in FIG. 10, sub-acute tamoxifen treatment up-regulated the mRNA levels of both PNPLA2 and Laminin receptors. However, the increase in PNPLA2 receptor was more pronounced than the increase in Laminin receptor. This suggests that following tamoxifen treatment, endogenous PEDF is more likely to bind PNPLA2 and induce cell survival than to promote anti-angiogenic activity through the Laminin receptor.

Exogenous PEDF Attenuates Tamoxifen-Induced Hyperplasia and VEGF Elevation

The ability of exogenous recombinant PEDF (rPEDF) to overcome the destructive effect of tamoxifen on uterine weight and VEGF expression was explored. Based on established regimen of rPEDF treatment in mice [Chuderland, D. et al. *The Journal of clinical endocrinology and metabolism* 98, E258-66 (2013); and Chuderland, D. et al. *Human reproduction* (Oxford, England) 0, 1-9 (2013)], rPEDF was administered at a dose of 10 mg/kg to the ovariectomized mice treated for 7 days with daily doses of tamoxifen. As demonstrated in FIGS. 11 and 12A-B, a significant decrease in uterine weight and uterine VEGF protein levels were observed in mice treated with tamoxifen+rPEDF as compared to tamoxifen alone, suggesting that rPEDF abrogated tamoxifen-induced uterine adverse effects, possibly by resisting tamoxifen-induced VEGF elevation.

The Effect of rPEDF on Signaling Pathways

Analyzing the effect of administration of rPEDF on the levels of AKT and JNK phosphorylation in the sub-acute tamoxifen model revealed a significant decrease in phosphorylation of AKT (FIGS. 13A-B) and increase in phosphorylation of JNK (FIG. 14A-B) in mice treated with tamoxifen+rPEDF when compared to mice treated with tamoxifen alone. Thus, treatment with rPEDF may reduce activation of cancer-associated signaling pathways.

Prolonged Tamoxifen Treatment Affects Uterine Weight and VEGF and PEDF Expression Cancer patients are treated daily with tamoxifen for a long period (up to 10 years). Therefore, to evaluate the effects of prolonged tamoxifen administration, mice were administered with tamoxifen (2.5 µg/mouse) 5 days per week for one month. As demonstrated in FIGS. 15 and 16A-C, prolonged tamoxifen treatment induced similar effects as the sub-acute treatment, i.e. increase in uterine weight (FIG. 15), up-regulation of VEGF protein level (FIG. 16A) and down-regulation of PEDF protein level (FIG. 16B). As a consequence, the VEGF/PEDF ratio was significantly increased (FIG. 16C), complementary with the sub-acute treatment model.

Furthermore, evaluation of PEDF's receptors expression after one month of tamoxifen treatment showed that the level of PNPLA2 was significantly increased, whereas that of Laminin receptor did not change significantly (FIG. 17); indicating that the dominance of the survival pathway is even more pronounces following long term tamoxifen treatment.

Prolonged Exogenous PEDF Attenuates Tamoxifen-Induced Hyperplasia, VEGF Elevation and Blood Vessel Density The ability of exogenous recombinant PEDF (rPEDF) to overcome the destructive effect of prolonged tamoxifen treatment on uterine weight and VEGF expression was explored. Preliminary analysis indicated that treatment with rPEDF was more effective when administered following a short period of initiation with tamoxifen (data not shown); therefore rPEDF was administered to mice starting on day 8 of tamoxifen treatment. As shown in FIG. 18 uterine weights were down-regulated in mice treated with tamoxifen+ rPEDF, though not statistically significant (p=0.2). The level of expression of uterine VEGF protein was significantly decreased in mice treated with tamoxifen+rPEDF when compared to mice treated with tamoxifen alone (FIGS. 19A-B), suggesting a durable effect of rPEDF on the uterus after one month of treatment.

In addition, immunohistochemical staining using CD34 as a marker for endothelial cells was utilized to evaluate vascular changes following treatment with tamoxifen and tamoxifen+rPEDF. As clearly shown in FIG. 20, treatment with tamoxifen alone induced a remarkable increase in the density of uterine blood vessels as compared to control and prolonged treatment with tamoxifen+rPEDF showed a decrease in CD34 staining as compared to tamoxifen alone.

Modulation of ERα Pattern of Expression

The expression level of hormone receptors is a key aspect in tamoxifen treatment for breast cancer. Estrogen receptor (ER) mediated-signaling pathways are of particular interest as tamoxifen can exert its activity through binding to ER and therefore, changes in ER expression level may alter the tissue's response to tamoxifen. Hence, in the next step the levels of the hormonal receptors ERα, ERfβ and progesterone receptor (PR) were determined in the sub-acute and prolonged in vivo tamoxifen treatments models. As shown in FIG. 21A, sub-acute tamoxifen treatment up-regulated the level of ERα mRNA, however had no significant effect on ERfβ and PR. As also evident from FIG. 21A, rPEDF administration was able to attenuate the sub-acute tamoxifen-induced reduction in ERα mRNA levels. Furthermore, the protein level of ERα showed a similar trend, though not statistically significant (FIG. 21B, p=0.1).

Prolonged tamoxifen treatment, as shown in FIG. 22A, up-regulated the mRNA expression of both ERα and ERβ, however had no significant effect on PR expression. As also evident in FIG. 22A, rPEDF administration was able to reverse the prolonged tamoxifen-induced reduction in ERα mRNA levels. The level of ERα protein expression was in correlation with its mRNA level, verifying the ability of rPEDF to down-regulate the expression of ERα protein (FIG. 22B). Taken together, rPEDF treatment caused a specific decrease in ERα uterine expression, without modifying the expression of ERfβ and PR. The decrease in ERα expression has dual relevance to tamoxifen-treated uteri; meaning that ER-related signaling, known to mediate hyperplastic responses, is diminished, and that tamoxifen molecule has less receptors to bind to in any given cell; thus reducing uterine response to tamoxifen.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating gonadal toxicity induced by an agent in a subject in need thereof, wherein said agent is a chemotherapy selected from the group consisting of mechlorethamine procarbazine cyclophosphamide, ifosfamide, busulfan, melphalan, chlorambucil, and chlormethine, doxorubicin, cisplatin, carboplatin, anthracycline antibiotics, alkylating agents, platinum-coordination complexes, epipodophyllotoxins and camptothecins, the method comprising:
   (a) administering to the subject a therapeutically effective amount of pigment epithelium-derived factor (PEDF) peptide; and
   (b) determining gonadal function in said subject, thereby treating the gonadal toxicity induced by the agent in the subject.

2. The method of claim 1, wherein said subject is a male.

3. The method of claim 2, wherein said male is at a reproductive-age.

4. The method of claim 2, wherein said male has not been subjected to semen collection.

5. A method of treating gonadal toxicity induced by an agent in a subject in need thereof, the method comprising:
   (a) administering to the subject a therapeutically effective amount of pigment epithelium-derived factor (PEDF) peptide; and
   (b) determining gonadal function in said subject, thereby treating the gonadal toxicity induced by the agent in the subject.

6. The method of claim 5, wherein said gonadal toxicity is selected from the group consisting of hypogonadism, reduced spermatogenesis, reduced ovulation, premature ovarian failure and sterility.

7. The method of claim 5, wherein said gonadal toxicity comprises reduced ovulation.

8. The method of claim 5, wherein said agent is selected from the group consisting of chemotherapy and radiotherapy.

9. The method of claim 8, wherein said chemotherapy is selected from the group consisting of tamoxifen, mechlorethamine procarbazine cyclophosphamide, ifosfamide, busulfan, melphalan, chlorambucil, chlormethine, doxorubicin, cisplatin and carboplatin.

10. The method of claim 8, wherein said chemotherapy is selected from the group consisting of tamoxifen, Alkylating agents, Procarbazine, Platinum analogs and anthracycline antibiotics.

11. The method of claim 8, wherein said chemotherapy is selected from the group consisting of tamoxifen, anthracycline antibiotics, alkylating agents, platinum-coordination complexes, epipodophyllotoxins and camptothecins.

12. The method of claim 8, wherein said chemotherapy is tamoxifen and/or doxorubicin.

13. The method of claim 5, wherein said agent induces oxidative stress.

14. The method of claim 5, wherein said subject is diagnosed with cancer.

15. The method claim 14, wherein said cancer is selected from the group consisting of testicular cancer, breast cancer, ovarian cancer, lymphoma and leukemia.

16. The method of claim 5, wherein said chemotherapy is administered in a maximum tolerated dose (MTD).

17. The method of claim 5, further comprising administering the agent to the subject.

18. The method of claim 17, wherein said administering said PEDF is effected concomitant with administering said agent.

19. The method of claim 17, wherein said administering said PEDF is following administration of said agent.

20. The method of claim 3, wherein said subject is a female.

21. The method of claim 20, wherein said female has not been subjected to oocyte retrieval.

22. A method of treating cancer in a subject in need thereof, the method comprising:
   (a) administering to the subject a therapeutically effective amount of tamoxifen and a therapeutically effective amount of pigment epithelium-derived factor (PEDF) peptide; and
   (b) determining uterine toxicity in said subject, thereby treating the cancer.

23. The method of claim 22, wherein said subject is at a reproductive-age.

24. The method of claim 22, wherein said subject is at the pre-menopausal period.

25. The method of claim 22, wherein said subject is at the post-menopausal period.

26. The method of claim 22, wherein said cancer is breast cancer.

27. The method of claim 22, wherein said administering said PEDF is effected concomitant with administering said tamoxifen.

28. The method of claim 22, wherein said administering said PEDF is following administration of said tamoxifen.

29. A method of treating tamoxifen-induced uterine toxicity in a subject in need thereof, the method comprising:
(a) administering to the subject a therapeutically effective amount of pigment epithelium-derived factor (PEDF) peptide; and
(b) determining uterine toxicity in said subject, thereby treating the tamoxifen-induced uterine toxicity in the subject.

30. The method of claim 29, wherein said subject is diagnosed with cancer.

* * * * *

SEQUENCE LISTING

<160> NUMBER OF SEQ ID NOS: 47

<210> SEQ ID NO 1
<211> LENGTH: 1542
<212> TYPE: DNA
<213> ORGANISM: Homo sapiens

<400> SEQUENCE: 1

| ggtcgcttta agaaaggagt agctgtaatc tgaagcctgc tggacgctgg attagaaggc | 60 |
| agcaaaaaaa gctctgtgct ggctggagcc ccctcagtgt gcaggcttag agggactagg | 120 |
| ctgggtgtgg agctgcagcg tatccacagg ccccaggatg caggccctgg tgctactcct | 180 |
| ctgcattgga gccctcctcg gcacagcag ctgccagaac cctgccagcc ccccggagga | 240 |
| gggctcccca gaccccgaca gcacaggggc gctggtggag gaggaggatc ctttcttcaa | 300 |
| agtccccgtg aacaagctgg cagcggctgt ctccaacttc ggctatgacc tgtaccgggt | 360 |
| gcgatccagc acgagcccca cgaccaacgt gctcctgtct cctctcagtg tggccacggc | 420 |
| cctctcggcc ctctcgctgg gagcggagca gcgaacagaa tccatcattc accgggctct | 480 |
| ctactatgac ttgatcagca gcccagacat ccatggtacc tataaggagc tccttgacac | 540 |
| ggtcactgcc ccccagaaga acctcaagag tgcctcccgg atcgtctttg agaagaagct | 600 |
| gcgcataaaa tccagctttg tggcacctct ggaaaagtca tatgggacca gcccagagt | 660 |
| cctgacgggc aaccctcgct tggacctgca agagatcaac aactgggtgc aggcgcagat | 720 |
| gaaagggaag ctcgccaggt ccacaaagga aattcccgat gagatcagca ttctccttct | 780 |
| cggtgtggcg cacttcaagg ggcagtgggt aacaaagttt gactccagaa agacttccct | 840 |
| cgaggatttc tacttggatg aagagaggac cgtgagggtc cccatgatgt cggaccctaa | 900 |
| ggctgtttta cgctatggct tggattcaga tctcagctgc aagattgccc agctgcccct | 960 |
| gaccggaagc atgagtatca tcttcttcct gccccctgaaa gtgacccaga atttgacctt | 1020 |
| gatagaggag agcctcacct ccgagttcat tcatgacata gaccgagaac tgaagaccgt | 1080 |
| gcaggcggtc ctcactgtcc ccaagctgaa gctgagttat gaaggcgaag tcaccaagtc | 1140 |
| cctgcaggag atgaagctgc aatccttgtt tgattcacca gactttagca agatcacagg | 1200 |
| caaacccatc aagctgactc aggtggaaca ccgggctggc tttgagtgga cagaggatgg | 1260 |
| ggcgggaacc accccccagcc cagggctgca gcctgcccac ctcaccttcc cgctggacta | 1320 |
| tcaccttaac cagcctttca tcttcgtact gagggacaca gacacagggg cccttctctt | 1380 |
| cattggcaag attctggacc ccagggggccc ctaatatccc agtttaatat ccaataccc | 1440 |
| tagaagaaaa cccgagggac agcagattcc acaggacacg aaggctgccc ctgtaaggtt | 1500 |
| tcaatgcata caataaaaga gctttatccc taacttctgt ta | 1542 |

<210> SEQ ID NO 2
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 2

| gtgaaggtcg gtgtgaacgg | 20 |

<210> SEQ ID NO 3
<211> LENGTH: 21
<212> TYPE: DNA
<213> ORGANISM: Artificial Sequence

```
<220> FEATURE:
<223> OTHER INFORMATION: Single strand DNA oligonucleotide

<400> SEQUENCE: 3
gtgatggcat ggactgtggt c                                           21

<210> SEQ ID NO 4
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 4
tgtggcctca ttcctcct                                               18

<210> SEQ ID NO 5
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 5
tgagaatggg gacactgt                                               18

<210> SEQ ID NO 6
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 6
ctcatggact gattatggac agga                                        24

<210> SEQ ID NO 7
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 7
gcaggtcagc aaagaactta tagcc                                       25

<210> SEQ ID NO 8
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 8
ttcacccgga gcagtgat                                               18

<210> SEQ ID NO 9
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 9
gcctccagaa ttgtgtttga g                                           21
```

```
<210> SEQ ID NO 10
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 10
ccaagtctct gcaggacatg aag                                              23

<210> SEQ ID NO 11
<211> LENGTH: 21
<212> TYPE: DNA
<213> ORGANISM: Artificial Sequence
<220> FEATURE:
<223> OTHER INFORMATION: Single strand DNA oligonucleotide

<400> SEQUENCE: 11
ggtttgccag taatcttgct g                                                21

<210> SEQ ID NO 12
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 12
aaccagttgt ggtgtcagga c                                                21

<210> SEQ ID NO 13
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 13
ccgccatgtt tcttagagtg agg                                              23

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
ccaccgtgta tgccttctcc                                                  20

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
agagggacgc gacattctca at                                               22

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide
```

```
<400> SEQUENCE: 16
tgtttcagac ggagagaacg tc                                              22

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
tgagaatggg gacactgtga tg                                              22

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
cctgggacct tcactaacca                                                 20

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
cagcatccac cacatcagac                                                 20

<210> SEQ ID NO 20
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 20
cttcagtgcc aacagcct                                                   18

<210> SEQ ID NO 21
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 21
gacagtctct ctcggccat                                                  19

<210> SEQ ID NO 22
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
gccaacctcc tgatgcttct tt                                              22

<210> SEQ ID NO 23
```

```
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 23
ttgtaccctc gaagcgtgtg a                                              21

<210> SEQ ID NO 24
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 24
ggtgggcctt cctaacgag                                                 19

<210> SEQ ID NO 25
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 25
gaccacatca ggctcaatgc t                                              21

<210> SEQ ID NO 26
<211> LENGTH: 1490
<212> TYPE: DNA
<213> ORGANISM: Homo sapiens

<400> SEQUENCE: 26
ggacgctgga ttagaaggca gcaaaaaaag atctgtgctg gctggagccc cctcagtgtg      60
caggcttaga gggactaggc tgggtgtgga gctgcagcgt atccacaggc cccaggatgc     120
aggccctggt gctactcctc tgcattggag ccctcctcgg gcacagcagc tgccagaacc     180
ctgccagccc cccggaggag ggctccccag accccgacag cacaggggcg ctggtggagg     240
aggaggatcc tttcttcaaa gtccccgtga caagctggc agcggctgtc tccaacttcg     300
gctatgacct gtaccgggtg cgatccagca tgagccccac gaccaacgtg ctcctgtctc     360
ctctcagtgt ggccacggcc ctctcggccc tctcgctggg agcggacgag cgaacagaat     420
ccatcattca ccgggctctc tactatgact tgatcagcag cccagacatc catggtacct     480
ataaggagct cctttgacacg gtcactgccc cccagaagaa cctcaagagt gcctcccgga     540
tcgtctttga gaagaagctr cgcataaaat ccagctttgt ggcacctctg aaaagtcat     600 atgggaccag gcccagagtc ctgacgggca accctcgctt ggacctgcaa gagatcaaca     660
actgggtgca ggcgcagatg aaagggaagc tcgccaggtc cacaaaggaa attcccgatg     720
agatcagcat tctccttctc ggtgtggcgc acttcaaggg gcagtgggta acaaagtttg     780
actccagaaa gacttccctc gaggatttct acttggatga agagaggacc gtgagggtcc     840
ccatgatgtc ggaccctaag gctgttttac gctatggctt ggattcagat ctcagctgca     900
agattgccca gctgcccttg accggaagca tgagtatcat cttcttcctg ccccctgaaag     960 tgacccagaa tttgaccttg atagaggaga gcctcacctc cgagttcatt catgacatag    1020
accgagaact gaagaccgtg caggcggtcc tcactgtccc caagctgaag ctgagttacg    1080
aaggcgaagt caccaagtcc ctgcaggaga tgaagctgca atccttgttt gattcaccag    1140
```

```
actttagcaa gatcacaggc aaacccatca agctgactca ggtggaacac cgggctggct    1200
ttgagtggaa cgaggatggg gcgggaacca cccccagccc agggctgcag cctgcccacc    1260
tcaccttccc gctggactat caccttaacc agcctttcat cttcgtactg agggacacag    1320
acacaggggc ccttctcttc attggcaaga ttctggaccc caggggcccc taatatccca    1380
gtttaatatt ccaataccct agaagaaaac ccgagggaca gcagattcca caggacacga    1440
aggctgcccc tgtaaggttt caatgcatac aataaaagag ctttatccct              1490
```

<210> SEQ ID NO 27
<211> LENGTH: 418
<212> TYPE: PRT
<213> ORGANISM: Homo sapiens

<400> SEQUENCE: 27

```
Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
                20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
    50                  55                  60

Leu Tyr Arg Val Arg Ser Ser Thr Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
    195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Lys Val Thr Gln Asn Leu Thr Leu
                275                 280                 285

Ile Glu Glu Ser Leu Thr Ser Glu Phe Ile His Asp Ile Asp Arg Glu
                290                 295                 300

Leu Lys Thr Val Gln Ala Val Leu Thr Val Pro Lys Leu Lys Leu Ser
```

```
        305                 310                 315                 320
Tyr Glu Gly Glu Val Thr Lys Ser Leu Gln Glu Met Lys Leu Gln Ser
                    325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
        370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                    405                 410                 415

Gly Pro

<210> SEQ ID NO 28
<211> LENGTH: 3677
<212> TYPE: DNA
<213> ORGANISM: Homo sapiens

<400> SEQUENCE: 28
```

| | | | | | |
|---|---|---|---|---|---|
| tcgcggaggc | ttggggcagc | cgggtagctc | ggaggtcgtg | gcgctggggg | ctagcaccag | 60 |
| cgctctgtcg | ggaggcgcag | cggttaggtg | gaccggtcag | cggactcacc | ggccagggcg | 120 |
| ctcggtgctg | gaatttgata | ttcattgatc | cgggttttat | ccctcttctt | ttttcttaaa | 180 |
| catttttttt | taaaactgta | ttgtttctcg | ttttaattta | tttttgcttg | ccattcccca | 240 |
| cttgaatcgg | gccgacggct | tggggagatt | gctctacttc | cccaaatcac | tgtggatttt | 300 |
| ggaaaccagc | agaagagga  | aagaggtagc | aagagctcca | gagagaagtc | gaggaagaga | 360 |
| gagacggggt | cagagagagc | gcgcgggcgt | gcgagcagcg | aaagcgacag | gggcaaagtg | 420 |
| agtgacctgc | ttttgggggt | gaccgccgga | gcgcggcgtg | agccctcccc | cttgggatcc | 480 |
| cgcagctgac | cagtcgcgct | gacggacaga | cagacagaca | ccgcccccag | cccagctac  | 540 |
| cacctcctcc | ccggccggcg | gcggacagtg | gacgcggcgg | cgagccgcgg | gcaggggccg | 600 |
| gagcccgcgc | ccggaggcgg | ggtggagggg | gtcgggctc  | gcggcgtcgc | actgaaactt | 660 |
| ttcgtccaac | ttctgggctg | ttctcgcttc | ggaggagccg | tggtccgcgc | ggggaagcc  | 720 |
| gagccgagcg | gagccgcgag | aagtgctagc | tcgggccggg | aggagccgca | gccggaggag | 780 |
| ggggaggagg | aagaagagaa | ggaagaggag | aggggggccgc | agtggcgact | cggcgctcgg | 840 |
| aagccgggct | catggacggg | tgaggcggcg | gtgtgcgcag | acagtgctcc | agccgcgcgc | 900 |
| gctccccagg | ccctggcccg | ggcctcgggc | cggggaggaa | gagtagctcg | ccgaggcgcc | 960 |
| gaggagagcg | ggccgcccca | cagcccgagc | cggagaggga | gcgcgagccg | cgccggcccc | 1020 |
| ggtcgggcct | ccgaaaccat | gaactttctg | ctgtcttggg | tgcattggag | ccttgccttg | 1080 |
| ctgctctacc | tccaccatgc | caagtggtcc | caggctgcac | ccatggcaga | aggaggaggg | 1140 |
| cagaatcatc | acgaagtggt | gaagttcatg | gatgtctatc | agcgcagcta | ctgccatcca | 1200 |
| atcgagaccc | tggtggacat | cttccaggag | taccctgatg | agatcgagta | catcttcaag | 1260 |
| ccatcctgtg | tgcccctgat | gcgatgcggg | ggctgctgca | atgacgaggg | cctggagtgt | 1320 |
| gtgcccactg | aggagtccaa | catcaccatg | cagattatgc | ggatcaaacc | tcaccaaggc | 1380 |
| cagcacatag | agagatgag  | cttcctacag | cacaacaaat | gtgaatgcag | accaaagaaa | 1440 |
| gatagagcaa | gacaagaaaa | aaaatcagtt | cgaggaaagg | gaaaggggca | aaaacgaaag | 1500 |

```
cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcaggggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca ttttattttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160 tattctttt ttaaattaac agtgctaatg ttattggtgt cttcactgga tgtatttgac    2220
tgctgtggac ttgagttggg aggggaatgt tcccactcag atcctgacag ggaagaggag    2280
gagatgagag actctggcat gatctttttt ttgtcccact tggtggggcc agggtcctct    2340
cccctgccca ggaatgtgca aggccagggc atggggcaa atatgaccca gttttgggaa    2400
caccgacaaa cccagccctg gcgctgagcc tctctacccc aggtcagacg gacagaaaga    2460
cagatcacag gtacagggat gaggacaccg gctctgacca ggagtttggg gagcttcagg    2520
acattgctgt gctttgggga ttccctccac atgctgcacg cgcatctcgc ccccaggggc    2580
actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctccccctt cctgggactc gccctcatcc tcttcctgct cccctttcctg    2760 gggtgcagcc taaaaggacc tatgtcctca caccattgaa accactagtt ctgtcccccc    2820
aggagacctg gttgtgtgtg tgtgagtggt tgaccttcct ccatcccctg gtccttccct    2880
tcccttcccg aggcacagag agacagggca ggatccacgt gcccattgtg gaggcagaga    2940
aaagagaaag tgttttatat acggtactta tttaatatcc cttttttaatt agaaattaaa    3000 acagttaatt taattaaaga gtagggtttt ttttcagtat tcttggttaa tatttaattt    3060 caactatta tgagatgtat cttttgctct ctcttgctct cttatttgta ccggtttttg    3120
tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tccttggaaa taaggttttca atatacatct acatactata tatatatttg    3300
gcaacttgta tttgtgtgta tatatatata tatgtttta tgtatatatg tgattctgat    3360
aaaatagaca ttgctattct gttttttata tgtaaaaaca aacaagaaa aaatagagaa    3420 ttctacatac taaatctctc tccttttttta attttaatat ttgttatcat ttatttattg    3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaaagcat tttgtattaa agaatttaat tctgatctca    3660
aaaaaaaaaa aaaaaaa                                                    3677
```

<210> SEQ ID NO 29
<211> LENGTH: 412
<212> TYPE: PRT

<213> ORGANISM: Homo sapiens

<400> SEQUENCE: 29

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
                35                  40                  45

Gly Val Ala Leu Lys Leu Phe Val Gln Leu Leu Gly Cys Ser Arg Phe
65              70                  75                  80

Gly Gly Ala Val Val Arg Ala Gly Glu Ala Pro Ser Gly Ala Ala
65              70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
                340                 345                 350

Leu Met Pro Trp Ser Leu Pro Gly Pro His Pro Cys Gly Pro Cys Ser
            355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400
```

```
Asn Glu Arg Thr Cys Arg Cys Asp Lys Pro Arg Arg
            405                 410
```

<210> SEQ ID NO 30
<211> LENGTH: 389
<212> TYPE: PRT
<213> ORGANISM: Homo sapiens

<400> SEQUENCE: 30

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Pro Cys Gly Pro Cys Ser Glu Arg Lys His Leu Phe
            340                 345                 350

Val Gln Asp Pro Gln Thr Cys Lys Cys Ser Cys Lys Asn Thr Asp Ser
        355                 360                 365
```

Arg Cys Lys Ala Arg Gln Leu Glu Leu Asn Glu Arg Thr Cys Arg Cys
        370                 375                 380

Asp Lys Pro Arg Arg
385

<210> SEQ ID NO 31
<211> LENGTH: 371
<212> TYPE: PRT
<213> ORGANISM: Homo sapiens

<400> SEQUENCE: 31

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys

```
                  340                 345                 350
Lys Ala Arg Gln Leu Glu Leu Asn Glu Arg Thr Cys Arg Cys Asp Lys
            355                 360                 365
Pro Arg Arg
    370

<210> SEQ ID NO 32
<211> LENGTH: 354
<212> TYPE: PRT
<213> ORGANISM: Homo sapiens

<400> SEQUENCE: 32

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335
```

Asp Pro Gln Thr Cys Lys Cys Ser Cys Lys Asn Thr Asp Ser Arg Cys
            340                 345                 350

Lys Met

<210> SEQ ID NO 33
<211> LENGTH: 327
<212> TYPE: PRT
<213> ORGANISM: Homo sapiens

<400> SEQUENCE: 33

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Cys Asp Lys Pro Arg Arg
                325

<210> SEQ ID NO 34
<211> LENGTH: 371

<212> TYPE: PRT
<213> ORGANISM: Homo sapiens

<400> SEQUENCE: 34

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
                35                  40                  45

Gly Val Ala Leu Lys Leu Phe Val Gln Leu Leu Gly Cys Ser Arg Phe
50                      55                      60

Gly Gly Ala Val Val Arg Ala Gly Glu Ala Glu Pro Ser Gly Ala Ala
65                      70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125

Ser Ala Pro Ala Ala Arg Ala Pro Gln Ala Leu Ala Arg Ala Ser Gly
                130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190

Ala Leu Leu Leu Tyr Leu His His Ala Lys Trp Ser Gln Ala Ala Pro
                195                 200                 205

Met Ala Glu Gly Gly Gly Gln Asn His His Glu Val Val Lys Phe Met
                210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
                275                 280                 285

Ile Lys Pro His Gln Gly Gln His Ile Gly Glu Met Ser Phe Leu Gln
                290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
                340                 345                 350

Lys Ala Arg Gln Leu Glu Leu Asn Glu Arg Thr Cys Arg Ser Leu Thr
                355                 360                 365

Arg Lys Asp
    370
```

<210> SEQ ID NO 35

```
<211> LENGTH: 317
<212> TYPE: PRT
<213> ORGANISM: Homo sapiens

<400> SEQUENCE: 35

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Cys Asp Lys Pro Arg Arg
305                 310                 315

<210> SEQ ID NO 36
<211> LENGTH: 232
<212> TYPE: PRT
<213> ORGANISM: Homo sapiens

<400> SEQUENCE: 36

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30
```

```
Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
210                 215                 220

Cys Arg Cys Asp Lys Pro Arg Arg
225                 230

<210> SEQ ID NO 37
<211> LENGTH: 215
<212> TYPE: PRT
<213> ORGANISM: Homo sapiens

<400> SEQUENCE: 37

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
```

```
                    165                 170                 175

Leu Phe Val Gln Asp Pro Gln Thr Cys Lys Cys Ser Cys Lys Asn Thr
                180                 185                 190

Asp Ser Arg Cys Lys Ala Arg Gln Leu Glu Leu Asn Glu Arg Thr Cys
            195                 200                 205

Arg Cys Asp Lys Pro Arg Arg
        210                 215

<210> SEQ ID NO 38
<211> LENGTH: 209
<212> TYPE: PRT
<213> ORGANISM: Homo sapiens

<400> SEQUENCE: 38

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Pro
145                 150                 155                 160

Cys Gly Pro Cys Ser Glu Arg Arg Lys His Leu Phe Val Gln Asp Pro
                165                 170                 175

Gln Thr Cys Lys Cys Ser Cys Lys Asn Thr Asp Ser Arg Cys Lys Ala
            180                 185                 190

Arg Gln Leu Glu Leu Asn Glu Arg Thr Cys Arg Cys Asp Lys Pro Arg
        195                 200                 205

Arg

<210> SEQ ID NO 39
<211> LENGTH: 191
<212> TYPE: PRT
<213> ORGANISM: Homo sapiens

<400> SEQUENCE: 39

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60
```

```
Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 40
<211> LENGTH: 174
<212> TYPE: PRT
<213> ORGANISM: Homo sapiens

<400> SEQUENCE: 40

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Met
                165                 170

<210> SEQ ID NO 41
<211> LENGTH: 147
<212> TYPE: PRT
<213> ORGANISM: Homo sapiens

<400> SEQUENCE: 41

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
            20                  25                  30
```

-continued

Gly Gly Gln Asn His His Glu Val Val Lys Phe Met Asp Val Tyr Gln
          35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
              85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Cys Asp Lys
130                 135                 140

Pro Arg Arg
145

<210> SEQ ID NO 42
<211> LENGTH: 191
<212> TYPE: PRT
<213> ORGANISM: Homo sapiens

<400> SEQUENCE: 42

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
          35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
              85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
            165                 170                 175

Leu Glu Leu Asn Glu Arg Thr Cys Arg Ser Leu Thr Arg Lys Asp
            180                 185                 190

<210> SEQ ID NO 43
<211> LENGTH: 137
<212> TYPE: PRT
<213> ORGANISM: Homo sapiens

<400> SEQUENCE: 43

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Cys Asp Lys Pro Arg Arg
    130                 135

<210> SEQ ID NO 44
<211> LENGTH: 171
<212> TYPE: PRT
<213> ORGANISM: Homo sapiens

<400> SEQUENCE: 44

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Cys Asp Lys Pro Arg Arg
                165                 170

<210> SEQ ID NO 45
<211> LENGTH: 351
<212> TYPE: PRT
<213> ORGANISM: Homo sapiens

<400> SEQUENCE: 45

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Glu Gly Val Gly Ala Arg
              35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Glu Arg Gly Pro Gln Trp Arg Leu Gly
             100                 105                 110

Ala Arg Lys Pro Gly Ser Trp Thr Gly Glu Ala Ala Val Cys Ala Asp
             115                 120                 125

Ser Ala Pro Ala Ala Arg Ala Pro Gln Ala Leu Ala Arg Ala Ser Gly
         130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                 165                 170                 175

Ala Ser Glu Thr Met Asn Phe Leu Leu Ser Trp Val His Trp Ser Leu
             180                 185                 190

Ala Leu Leu Leu Tyr Leu His His Ala Lys Trp Ser Gln Ala Ala Pro
             195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                 245                 250                 255

Cys Val Pro Leu Met Arg Cys Gly Gly Cys Cys Asn Asp Glu Gly Leu
             260                 265                 270

Glu Cys Val Pro Thr Glu Glu Ser Asn Ile Thr Met Gln Ile Met Arg
         275                 280                 285

Ile Lys Pro His Gln Gly Gln His Ile Gly Glu Met Ser Phe Leu Gln
     290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                 325                 330                 335

Lys Ser Arg Tyr Lys Ser Trp Ser Val Cys Asp Lys Pro Arg Arg
             340                 345                 350

<210> SEQ ID NO 46
<211> LENGTH: 163
<212> TYPE: PRT
<213> ORGANISM: Homo sapiens

<400> SEQUENCE: 46

Met Ala Glu Gly Gly Gly Gln Asn His His Glu Val Val Lys Phe Met
1               5                   10                  15

Asp Val Tyr Gln Arg Ser Tyr Cys His Pro Ile Glu Thr Leu Val Asp
                 20                  25                  30

Ile Phe Gln Glu Tyr Pro Asp Glu Ile Glu Tyr Ile Phe Lys Pro Ser
             35                  40                  45

Cys Val Pro Leu Met Arg Cys Gly Gly Cys Cys Asn Asp Glu Gly Leu

```
                    50                  55                  60
Glu Cys Val Pro Thr Glu Ser Asn Ile Thr Met Gln Ile Met Arg
 65                  70                  75                  80

Ile Lys Pro His Gln Gly Gln His Ile Gly Glu Met Ser Phe Leu Gln
                 85                  90                  95

His Asn Lys Cys Glu Cys Arg Pro Lys Lys Asp Arg Ala Arg Gln Glu
                100                 105                 110

Asn Pro Cys Gly Pro Cys Ser Glu Arg Arg Lys His Leu Phe Val Gln
                115                 120                 125

Asp Pro Gln Thr Cys Lys Cys Ser Cys Lys Asn Thr Asp Ser Arg Cys
                130                 135                 140

Lys Ala Arg Gln Leu Glu Leu Asn Glu Arg Thr Cys Arg Cys Asp Lys
145                 150                 155                 160

Pro Arg Arg

<210> SEQ ID NO 47
<211> LENGTH: 395
<212> TYPE: PRT
<213> ORGANISM: Homo sapiens

<400> SEQUENCE: 47

Met Thr Asp Arg Gln Thr Asp Thr Ala Pro Ser Pro Ser Tyr His Leu
 1               5                  10                  15

Leu Pro Gly Arg Arg Thr Val Asp Ala Ala Ala Ser Arg Gly Gln
                 20                  25                  30

Gly Pro Glu Pro Ala Pro Gly Gly Val Glu Gly Val Gly Ala Arg
                 35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125

Ser Ala Pro Ala Ala Arg Ala Pro Gln Ala Leu Ala Arg Ala Ser Gly
                130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190

Ala Leu Leu Leu Tyr Leu His His Ala Lys Trp Ser Gln Ala Ala Pro
                195                 200                 205

Met Ala Glu Gly Gly Gly Gln Asn His His Glu Val Val Lys Phe Met
                210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
```

-continued

```
                260                 265                 270
Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Pro Cys Gly Pro Cys Ser Glu
            340                 345                 350

Arg Arg Lys His Leu Phe Val Gln Asp Pro Gln Thr Cys Lys Cys Ser
        355                 360                 365

Cys Lys Asn Thr Asp Ser Arg Cys Lys Ala Arg Gln Leu Glu Leu Asn
        370                 375                 380

Glu Arg Thr Cys Arg Cys Asp Lys Pro Arg Arg
385                 390                 395
```